United States Patent
de Juan, Jr. et al.

(10) Patent No.: US 10,010,448 B2
(45) Date of Patent: Jul. 3, 2018

(54) INSERTION AND REMOVAL METHODS AND APPARATUS FOR THERAPEUTIC DEVICES

(71) Applicant: ForSight Vision4, Inc., Menlo Park, CA (US)

(72) Inventors: Eugene de Juan, Jr., Menlo Park, CA (US); Randolph E. Campbell, Menlo Park, CA (US); Signe Erickson, Menlo Park, CA (US); Mike Barrett, Menlo Park, CA (US); Christina Skieller, Menlo Park, CA (US); David Batten, Menlo Park, CA (US); Darren Doud, Menlo Park, CA (US)

(73) Assignee: ForSight Vision4, Inc., Menlo Park, CA (US)

(*) Notice: Subject to any disclaimer, the term of this patent is extended or adjusted under 35 U.S.C. 154(b) by 610 days.

(21) Appl. No.: 14/376,331

(22) PCT Filed: Jan. 23, 2013

(86) PCT No.: PCT/US2013/022770
§ 371 (c)(1),
(2) Date: Aug. 1, 2014

(87) PCT Pub. No.: WO2013/116061
PCT Pub. Date: Aug. 8, 2013

(65) Prior Publication Data
US 2015/0080846 A1 Mar. 19, 2015

Related U.S. Application Data

(60) Provisional application No. 61/594,961, filed on Feb. 3, 2012.

(51) Int. Cl.
*A61F 9/00* (2006.01)
*A61K 9/00* (2006.01)
(Continued)

(52) U.S. Cl.
CPC ........ *A61F 9/0017* (2013.01); *A61F 9/00772* (2013.01); *A61K 9/0051* (2013.01);
(Continued)

(58) Field of Classification Search
CPC ............... A61F 9/00772; A61F 9/0017; A61F 2220/0033; A61F 2220/0008; A61K 9/0051; A61M 37/0069
See application file for complete search history.

(56) References Cited

U.S. PATENT DOCUMENTS 2,564,977 A 8/1951 Hu et al.
2,585,815 A 2/1952 McLintock
(Continued)

FOREIGN PATENT DOCUMENTS

EP 0 228 185 A1 11/1986
EP 0498471 A2 8/1992
(Continued)

OTHER PUBLICATIONS

Andrews, "Effect of nonsteroidal anti-inflammatory drugs on LFA-1 and ICAM-1 expression in gastric mucosa," Am J Physiol. Apr. 1994;266(4 Pt 1):G657-664.
(Continued)

*Primary Examiner* — Nathan R Price
*Assistant Examiner* — Anh Bui
(74) *Attorney, Agent, or Firm* — Mintz Levin Cohn Ferris Glovsky and Popeo, P.C.

(57) ABSTRACT

Described herein is an apparatus to insert an implantable therapeutic device into a patient. The apparatus includes a proximal handle (210) and a distal placement portion (220) coupled to the proximal handle and configured to hold the implantable therapeutic device. The distal placement portion includes a first side (222) having a first engagement structure (251) at a distal end of the first side, the first engagement
(Continued)

structure configured to surround at least a first portion of a proximal end region of the implantable therapeutic device. The distal placement portion includes a second, opposite side (224) having a second engagement structure (253) at a distal end of the second side, the second engagement structure configured to surround at least a second, opposite portion of the proximal end region of the implantable therapeutic device.

21 Claims, 20 Drawing Sheets

(51) Int. Cl.
    *A61F 9/007*     (2006.01)
    *A61M 37/00*     (2006.01)

(52) U.S. Cl.
    CPC ............... *A61F 2220/0008* (2013.01); *A61F 2220/0033* (2013.01); *A61F 2250/0068* (2013.01); *A61M 37/0069* (2013.01)

(56) References Cited

U.S. PATENT DOCUMENTS

| | | |
|---|---|---|
| 3,232,117 A | 2/1966 | Gilmont |
| 3,416,530 A | 12/1968 | Ness |
| 3,618,604 A | 11/1971 | Ness |
| 3,641,237 A | 2/1972 | Gould et al. |
| 3,828,777 A | 8/1974 | Ness |
| 3,902,495 A | 9/1975 | Weiss et al. |
| 3,916,899 A | 11/1975 | Theeuwes et al. |
| 3,949,748 A | 4/1976 | Malmin |
| 3,949,750 A | 4/1976 | Freeman |
| 3,961,628 A | 6/1976 | Arnold |
| 3,977,404 A | 8/1976 | Theeuwes |
| 3,995,635 A | 12/1976 | Higuchi et al. |
| 4,008,719 A | 2/1977 | Theeuwes et al. |
| 4,014,333 A | 3/1977 | McIntyre |
| 4,014,334 A | 3/1977 | Theeuwes et al. |
| 4,014,335 A | 3/1977 | Arnold |
| 4,034,756 A | 7/1977 | Higuchi et al. |
| 4,034,758 A | 7/1977 | Theeuwes |
| 4,077,407 A | 3/1978 | Theeuwes et al. |
| 4,111,201 A | 9/1978 | Theeuwes |
| 4,111,203 A | 9/1978 | Theeuwes |
| 4,135,514 A | 1/1979 | Zaffaroni et al. |
| 4,160,452 A | 7/1979 | Theeuwes |
| 4,200,098 A | 4/1980 | Ayer et al. |
| 4,220,152 A | 9/1980 | Dresback |
| 4,220,153 A | 9/1980 | Dresback |
| 4,256,108 A | 3/1981 | Theeuwes |
| 4,298,000 A | 11/1981 | Thill et al. |
| 4,300,557 A | 11/1981 | Refojo et al. |
| 4,309,776 A | 1/1982 | Berguer |
| 4,326,525 A | 4/1982 | Swanson et al. |
| 4,327,725 A | 5/1982 | Cortese et al. |
| 4,439,196 A | 3/1984 | Higuchi |
| 4,475,916 A | 10/1984 | Himmelstein |
| 4,484,922 A | 11/1984 | Rosenwald |
| 4,519,801 A | 5/1985 | Edgren |
| 4,609,374 A | 9/1986 | Ayer |
| 4,627,850 A | 12/1986 | Deters et al. |
| 4,673,405 A | 6/1987 | Guittard et al. |
| 4,693,886 A | 9/1987 | Ayer |
| 4,712,550 A | 12/1987 | Sinnett |
| 4,737,150 A | 4/1988 | Baeumle et al. |
| 4,777,049 A | 10/1988 | Magruder et al. |
| 4,781,675 A | 11/1988 | White |
| 4,863,457 A | 9/1989 | Lee |
| 4,865,846 A | 9/1989 | Kaufman |
| 4,883,459 A | 11/1989 | Calderon |
| 4,959,217 A | 9/1990 | Sanders et al. |
| 5,084,021 A | 1/1992 | Baldwin |
| 5,098,443 A | 3/1992 | Parel et al. |
| 5,128,145 A | 7/1992 | Edgren et al. |
| 5,164,188 A | 11/1992 | Wong |
| 5,174,999 A | 12/1992 | Magruder et al. |
| 5,178,622 A | 1/1993 | Lehner, II |
| 5,277,912 A | 1/1994 | Lowe et al. |
| 5,282,829 A | 2/1994 | Hermes |
| 5,300,114 A | 4/1994 | Gwon et al. |
| 5,322,691 A | 6/1994 | Darougar et al. |
| 5,334,189 A | 8/1994 | Wade |
| 5,336,175 A | 8/1994 | Mames |
| 5,378,475 A | 1/1995 | Smith et al. |
| 5,413,572 A | 5/1995 | Wong et al. |
| 5,443,505 A | 8/1995 | Wong et al. |
| 5,476,511 A | 12/1995 | Gwon et al. |
| 5,516,522 A | 5/1996 | Peyman et al. |
| 5,554,132 A | 9/1996 | Straits et al. |
| 5,562,915 A | 10/1996 | Lowe et al. |
| 5,681,572 A | 10/1997 | Seare, Jr. |
| 5,702,414 A | 12/1997 | Richter et al. |
| 5,766,242 A | 6/1998 | Wong et al. |
| 5,770,076 A | 6/1998 | Chu et al. |
| 5,773,019 A | 6/1998 | Ashton et al. |
| 5,797,898 A | 8/1998 | Santini, Jr. et al. |
| 5,807,581 A | 9/1998 | Rosenblatt et al. |
| 5,824,072 A | 10/1998 | Wong |
| 5,830,173 A | 11/1998 | Avery et al. |
| 5,830,546 A | 11/1998 | Ehret et al. |
| 5,836,935 A | 11/1998 | Ashton et al. |
| 5,868,697 A | 2/1999 | Richter et al. |
| 5,902,598 A | 5/1999 | Chen et al. |
| 5,916,584 A | 6/1999 | O'Donoghue et al. |
| 5,928,662 A | 7/1999 | Phillips |
| 5,951,512 A | 9/1999 | Dalton |
| 5,972,369 A | 10/1999 | Roorda et al. |
| 5,985,328 A | 11/1999 | Chu et al. |
| 6,001,386 A | 12/1999 | Ashton et al. |
| 6,039,712 A * | 3/2000 | Fogarty ............ A61M 39/0208 604/175 |
| 6,096,070 A | 8/2000 | Ragheb et al. |
| 6,123,861 A | 9/2000 | Santini, Jr. et al. |
| 6,196,993 B1 | 3/2001 | Cohan et al. |
| 6,303,290 B1 | 10/2001 | Liu et al. |
| 6,331,313 B1 | 12/2001 | Wong et al. |
| 6,375,972 B1 | 4/2002 | Guo et al. |
| 6,395,300 B1 | 5/2002 | Straub et al. |
| 6,413,540 B1 | 7/2002 | Yaacobi |
| 6,416,777 B1 | 7/2002 | Yaacobi |
| 6,420,399 B1 | 7/2002 | Graff et al. |
| 6,472,162 B1 | 10/2002 | Coelho et al. |
| 6,605,066 B1 | 8/2003 | Gravagna et al. |
| 6,663,668 B1 | 12/2003 | Chaouk et al. |
| 6,669,950 B2 | 12/2003 | Yaacobi |
| 6,685,940 B2 | 2/2004 | Andya et al. |
| 6,713,081 B2 | 3/2004 | Robinson et al. |
| 6,719,750 B2 | 4/2004 | Varner et al. |
| 6,740,077 B1 | 5/2004 | Brandau et al. |
| 6,756,049 B2 | 6/2004 | Brubaker et al. |
| 6,756,058 B2 | 6/2004 | Brubaker et al. |
| 6,932,983 B1 | 8/2005 | Straub et al. |
| 6,976,982 B2 | 12/2005 | Santini, Jr. et al. |
| 6,986,900 B2 | 1/2006 | Yaacobi |
| 7,026,329 B2 | 4/2006 | Crain et al. |
| 7,074,426 B2 | 7/2006 | Kochinke |
| 7,077,848 B1 | 7/2006 | de Juan, Jr. et al. |
| 7,090,681 B2 | 8/2006 | Weber et al. |
| 7,094,226 B2 | 8/2006 | Yaacobi |
| 7,117,870 B2 | 10/2006 | Prescott |
| 7,141,152 B2 | 11/2006 | Le Febre |
| 7,181,287 B2 | 2/2007 | Greenberg |
| 7,195,774 B2 | 3/2007 | Carvalho et al. |
| 7,195,778 B2 | 3/2007 | Fleshner-Barak et al. |
| 7,211,272 B2 | 5/2007 | Renner et al. |
| 7,276,050 B2 | 10/2007 | Franklin |
| 7,468,065 B2 | 12/2008 | Weber et al. |
| 7,476,510 B2 | 1/2009 | Kapur et al. |
| 7,585,517 B2 | 9/2009 | Cooper et al. |
| 7,615,141 B2 | 11/2009 | Schwartz et al. |
| 7,621,907 B2 | 11/2009 | Rodstrom |

(56) References Cited

U.S. PATENT DOCUMENTS

| | | |
|---|---|---|
| 7,625,927 B2 | 12/2009 | Klimko et al. |
| 7,678,078 B1 | 3/2010 | Peyman et al. |
| 7,686,016 B2 | 3/2010 | Wharton et al. |
| 7,709,049 B2 | 5/2010 | Chappa |
| 7,883,717 B2 | 2/2011 | Varner et al. |
| 7,893,040 B2 | 2/2011 | Loftsson et al. |
| 7,906,136 B2 | 3/2011 | Wong et al. |
| 7,909,800 B2 | 3/2011 | Cazzini |
| 7,914,442 B1 | 3/2011 | Gazdzinski |
| 7,939,094 B2 | 5/2011 | Schwarz et al. |
| 7,973,068 B2 | 7/2011 | Demopulos et al. |
| 8,403,941 B2 | 3/2013 | Peterson et al. |
| 2002/0026176 A1 | 2/2002 | Varner et al. |
| 2002/0086051 A1 | 7/2002 | Viscasillas |
| 2002/0106395 A1 | 8/2002 | Brubaker |
| 2002/0110591 A1 | 8/2002 | Brubaker et al. |
| 2002/0110592 A1 | 8/2002 | Brubaker et al. |
| 2002/0110635 A1 | 8/2002 | Brubaker et al. |
| 2003/0003129 A1 | 1/2003 | Yaacobi |
| 2003/0005945 A1 | 1/2003 | Onishi et al. |
| 2003/0014036 A1 | 1/2003 | Varner et al. |
| 2003/0118649 A1 | 6/2003 | Gao et al. |
| 2003/0119177 A1 | 6/2003 | Gruber et al. |
| 2003/0176854 A1 | 9/2003 | Rodstrom |
| 2003/0185872 A1 | 10/2003 | Kochinke |
| 2003/0212383 A1 | 11/2003 | Cote et al. |
| 2003/0235603 A1 | 12/2003 | Schwarz et al. |
| 2004/0011651 A1 | 1/2004 | Becker et al. |
| 2004/0019325 A1 | 1/2004 | Shekalim |
| 2004/0092911 A1 | 5/2004 | Yaacobi |
| 2004/0106906 A1 | 6/2004 | Yaacobi |
| 2004/0131654 A1 | 7/2004 | Yaacobi |
| 2004/0131655 A1 | 7/2004 | Yaacobi |
| 2004/0209359 A1 | 10/2004 | Yayon et al. |
| 2004/0230183 A1 | 11/2004 | Breegi et al. |
| 2004/0260380 A1 | 12/2004 | Marco et al. |
| 2004/0260381 A1 | 12/2004 | Marco et al. |
| 2005/0064010 A1 | 3/2005 | Cooper et al. |
| 2005/0074497 A1 | 4/2005 | Schultz |
| 2005/0112175 A1 | 5/2005 | Yaacobi |
| 2005/0112759 A1 | 5/2005 | Radisic et al. |
| 2005/0113806 A1 | 5/2005 | De Carvalho et al. |
| 2005/0119737 A1 | 6/2005 | Bene et al. |
| 2005/0143363 A1 | 6/2005 | De Juan et al. |
| 2005/0154399 A1 | 7/2005 | Weber et al. |
| 2005/0163711 A1 | 7/2005 | Nycz et al. |
| 2005/0181018 A1 | 8/2005 | Peyman |
| 2005/0244467 A1 | 11/2005 | Nivaggioli et al. |
| 2005/0244469 A1 | 11/2005 | Whitcup et al. |
| 2005/0255144 A1 | 11/2005 | Schultz |
| 2005/0256499 A1 | 11/2005 | Pettis et al. |
| 2005/0271703 A1 | 12/2005 | Anderson et al. |
| 2005/0271706 A1 | 12/2005 | Anderson et al. |
| 2005/0276837 A1 | 12/2005 | Anderson et al. |
| 2005/0277802 A1 | 12/2005 | Larsen et al. |
| 2005/0281861 A1 | 12/2005 | Hughes et al. |
| 2005/0281863 A1 | 12/2005 | Anderson et al. |
| 2005/0287188 A1 | 12/2005 | Anderson et al. |
| 2006/0013835 A1 | 1/2006 | Anderson et al. |
| 2006/0039952 A1 | 2/2006 | Yaacobi |
| 2006/0052754 A1 | 3/2006 | Fields |
| 2006/0057277 A1 | 3/2006 | Chappa |
| 2006/0073182 A1 | 4/2006 | Wong et al. |
| 2006/0104969 A1 | 5/2006 | Oray et al. |
| 2006/0110428 A1 | 5/2006 | deJuan et al. |
| 2006/0129215 A1 | 6/2006 | Helmus et al. |
| 2006/0154981 A1 | 7/2006 | Klimko et al. |
| 2006/0172941 A1 | 8/2006 | Rastelli et al. |
| 2006/0182783 A1 | 8/2006 | Hughes et al. |
| 2006/0200097 A1 | 9/2006 | Humayun et al. |
| 2006/0233858 A1 | 10/2006 | Tzekov et al. |
| 2006/0246112 A1 | 11/2006 | Snyder et al. |
| 2006/0257450 A1 | 11/2006 | Mudumba et al. |
| 2006/0258000 A1 | 11/2006 | Allen et al. |
| 2006/0258994 A1 | 11/2006 | Avery |
| 2006/0276738 A1 | 12/2006 | Becker |
| 2007/0020336 A1 | 1/2007 | Loftsson et al. |
| 2007/0021357 A1 | 1/2007 | Tobia et al. |
| 2007/0026037 A1 | 2/2007 | Kloke et al. |
| 2007/0059336 A1 | 3/2007 | Hughes et al. |
| 2007/0071756 A1 | 3/2007 | Peyman |
| 2007/0072933 A1 | 3/2007 | Peyman |
| 2007/0077270 A1 | 4/2007 | Wen |
| 2007/0088414 A1 | 4/2007 | Campbell et al. |
| 2007/0119450 A1 | 5/2007 | Wharton et al. |
| 2007/0128644 A1 | 6/2007 | Munenaka |
| 2007/0131610 A1 | 6/2007 | Peng et al. |
| 2007/0131611 A1 | 6/2007 | Peng et al. |
| 2007/0134305 A1 | 6/2007 | Zilberman |
| 2007/0141111 A1 | 6/2007 | Suokas et al. |
| 2007/0191863 A1 | 8/2007 | De Juan et al. |
| 2007/0197491 A1 | 8/2007 | Robin et al. |
| 2007/0203174 A1 | 8/2007 | Klimko et al. |
| 2007/0212397 A1 | 9/2007 | Roth |
| 2007/0233037 A1 | 10/2007 | Gifford et al. |
| 2007/0235331 A1 | 10/2007 | Simpson et al. |
| 2007/0243230 A1 | 10/2007 | de Juan et al. |
| 2007/0260201 A1 | 11/2007 | Prausnitz et al. |
| 2007/0269487 A1 | 11/2007 | de Juan et al. |
| 2008/0003219 A1 | 1/2008 | Peyman |
| 2008/0004329 A1 | 1/2008 | Jamieson et al. |
| 2008/0020045 A1 | 1/2008 | Chappa et al. |
| 2008/0038316 A1 | 2/2008 | Wong et al. |
| 2008/0057561 A1 | 3/2008 | Takahashi et al. |
| 2008/0066739 A1 | 3/2008 | LeMahieu et al. |
| 2008/0066741 A1 | 3/2008 | LeMahieu et al. |
| 2008/0069854 A1 | 3/2008 | Xiao et al. |
| 2008/0089923 A1 | 4/2008 | Burkstrand et al. |
| 2008/0097459 A1 | 4/2008 | Kammerlander et al. |
| 2008/0111282 A1 | 5/2008 | Xie et al. |
| 2008/0124372 A1 | 5/2008 | Hossainy et al. |
| 2008/0139674 A1 | 6/2008 | Archambeau et al. |
| 2008/0145406 A1 | 6/2008 | Asgharian et al. |
| 2008/0146679 A1 | 6/2008 | Archambeau et al. |
| 2008/0147021 A1 | 6/2008 | Jani |
| 2008/0152694 A1 | 6/2008 | Lobl et al. |
| 2008/0154241 A1 | 6/2008 | Burkstrand et al. |
| 2008/0161741 A1 | 7/2008 | Bene et al. |
| 2008/0167600 A1 | 7/2008 | Peyman |
| 2008/0172014 A1 | 7/2008 | Whitcup et al. |
| 2008/0181930 A1 | 7/2008 | Rodstrom et al. |
| 2008/0207502 A1 | 8/2008 | Rastelli et al. |
| 2008/0213611 A1 | 9/2008 | Asgari |
| 2008/0216736 A1 | 9/2008 | David |
| 2008/0228127 A1 | 9/2008 | Burns et al. |
| 2008/0233053 A1 | 9/2008 | Gross et al. |
| 2008/0233171 A1 | 9/2008 | Whitcup et al. |
| 2008/0233172 A1 | 9/2008 | Whitcup et al. |
| 2008/0233173 A1 | 9/2008 | Whitcup et al. |
| 2008/0241219 A1 | 10/2008 | Whitcup et al. |
| 2008/0241220 A1 | 10/2008 | Whitcup et al. |
| 2008/0241221 A1 | 10/2008 | Whitcup et al. |
| 2008/0241222 A1 | 10/2008 | Whitcup et al. |
| 2008/0241223 A1 | 10/2008 | Nivaggioli et al. |
| 2008/0249501 A1 | 10/2008 | Yamasaki |
| 2008/0286338 A1 | 11/2008 | Rosenthal et al. |
| 2008/0292679 A1 | 11/2008 | Lyons et al. |
| 2009/0005864 A1 | 1/2009 | Eggleston |
| 2009/0036827 A1 | 2/2009 | Cazzini |
| 2009/0043253 A1 | 2/2009 | Podaima |
| 2009/0047335 A1 | 2/2009 | Rastelli et al. |
| 2009/0082631 A1 | 3/2009 | Cronin et al. |
| 2009/0087494 A1 | 4/2009 | Kompella et al. |
| 2009/0092654 A1 | 4/2009 | de Juan, Jr. et al. |
| 2009/0093752 A1 | 4/2009 | Richard et al. |
| 2009/0099626 A1 | 4/2009 | de Juan, Jr. et al. |
| 2009/0104243 A1 | 4/2009 | Utkhede et al. |
| 2009/0105749 A1 | 4/2009 | de Juan et al. |
| 2009/0124997 A1 | 5/2009 | Pettis et al. |
| 2009/0214601 A1 | 8/2009 | Chappa et al. |
| 2009/0224064 A1 | 9/2009 | Brodbeck et al. |
| 2009/0234449 A1 | 9/2009 | De Juan, Jr. et al. |
| 2009/0240215 A1 | 9/2009 | Humayun et al. |
| 2009/0247458 A1 | 10/2009 | Watson et al. |

(56) References Cited

U.S. PATENT DOCUMENTS

| | | |
|---|---|---|
| 2009/0258069 A1 | 10/2009 | Burnier et al. |
| 2009/0263346 A1 | 10/2009 | Taft et al. |
| 2009/0263495 A1 | 10/2009 | Watson et al. |
| 2009/0274730 A1 | 11/2009 | Watson et al. |
| 2009/0274771 A1 | 11/2009 | Watson et al. |
| 2009/0280470 A1 | 11/2009 | Fare et al. |
| 2009/0281621 A1 | 11/2009 | Becker |
| 2009/0324686 A1 | 12/2009 | Cooper et al. |
| 2009/0324687 A1 | 12/2009 | Cooper et al. |
| 2009/0324688 A1 | 12/2009 | Cooper et al. |
| 2009/0324689 A1 | 12/2009 | Cooper et al. |
| 2009/0324690 A1 | 12/2009 | Cooper et al. |
| 2009/0326448 A1 | 12/2009 | Huo et al. |
| 2010/0003333 A1 | 1/2010 | Watson et al. |
| 2010/0004189 A1 | 1/2010 | Watson et al. |
| 2010/0008997 A1 | 1/2010 | Watson et al. |
| 2010/0009008 A1 | 1/2010 | Watson et al. |
| 2010/0010452 A1 | 1/2010 | Paques et al. |
| 2010/0011888 A1 | 1/2010 | Pawliszyn et al. |
| 2010/0015157 A1 | 1/2010 | Andya et al. |
| 2010/0016786 A1 | 1/2010 | Drews et al. |
| 2010/0021464 A1 | 1/2010 | Archambeau et al. |
| 2010/0022943 A1 | 1/2010 | Mauch et al. |
| 2010/0022945 A1 | 1/2010 | Rodstrom |
| 2010/0023033 A1 | 1/2010 | Mauch et al. |
| 2010/0028442 A1 | 2/2010 | Archambeau et al. |
| 2010/0028443 A1 | 2/2010 | Watson et al. |
| 2010/0030136 A1 | 2/2010 | Dacquay et al. |
| 2010/0034870 A1 | 2/2010 | Sim et al. |
| 2010/0083963 A1 | 4/2010 | Wharton et al. |
| 2010/0100054 A1 | 4/2010 | Cormier et al. |
| 2010/0114017 A1 | 5/2010 | Lenker et al. |
| 2010/0114309 A1 | 5/2010 | de Juan, Jr. et al. |
| 2010/0168535 A1 | 7/2010 | Robinson et al. |
| 2010/0174272 A1 | 7/2010 | Weiner |
| 2010/0185205 A1 | 7/2010 | Novakovic et al. |
| 2010/0197512 A1 | 8/2010 | Trinkle et al. |
| 2010/0216702 A1 | 8/2010 | Szkudlinski et al. |
| 2010/0221309 A1 | 9/2010 | Myers et al. |
| 2010/0255061 A1 | 10/2010 | de Juan, Jr. et al. |
| 2010/0256597 A1 | 10/2010 | Prausnitz et al. |
| 2010/0266664 A1 | 10/2010 | Asgharian et al. |
| 2010/0286121 A1 | 11/2010 | Rohrs et al. |
| 2010/0286791 A1 | 11/2010 | Goldsmith |
| 2010/0297046 A1 | 11/2010 | Schwartz et al. |
| 2010/0297120 A1 | 11/2010 | Beliveau et al. |
| 2010/0297193 A1 | 11/2010 | Archambeau et al. |
| 2010/0303917 A1 | 12/2010 | Watson et al. |
| 2010/0303918 A1 | 12/2010 | Watson et al. |
| 2010/0310664 A1 | 12/2010 | Watson et al. |
| 2010/0310665 A1 | 12/2010 | Watson et al. |
| 2010/0316723 A1 | 12/2010 | Watson et al. |
| 2010/0330146 A1 | 12/2010 | Chauhan et al. |
| 2011/0009571 A1 | 1/2011 | Taft et al. |
| 2011/0014264 A1 | 1/2011 | Helmus et al. |
| 2011/0033933 A1 | 2/2011 | Gharib et al. |
| 2011/0034448 A1 | 2/2011 | Chang et al. |
| 2011/0081384 A1 | 4/2011 | Archambeau et al. |
| 2011/0098686 A1 | 4/2011 | Varner et al. |
| 2011/0104155 A1 | 5/2011 | Rekik |
| 2011/0108025 A1 | 5/2011 | Fink et al. |
| 2011/0111006 A1 | 5/2011 | Wong et al. |
| 2011/0112188 A1 | 5/2011 | Tobia et al. |
| 2011/0117083 A1 | 5/2011 | Bais et al. |
| 2011/0125178 A1 | 5/2011 | Drews et al. |
| 2011/0159073 A1 | 6/2011 | deJuan et al. |
| 2011/0196317 A1* | 8/2011 | Lust ............... A61B 50/30 604/290 |
| 2011/0206646 A1 | 8/2011 | Alfonso et al. |
| 2012/0029445 A1 | 2/2012 | de Juan, Jr. et al. |
| 2012/0029470 A1 | 2/2012 | Juan, Jr. et al. |
| 2012/0245505 A1 | 9/2012 | Robinson et al. |
| 2014/0379079 A1* | 12/2014 | Ben Nun ............ A61F 2/1613 623/6.37 |

FOREIGN PATENT DOCUMENTS

| | | |
|---|---|---|
| EP | 0500143 A2 | 8/1992 |
| EP | 0671165 A2 | 9/1995 |
| EP | 0295248 B2 | 4/1999 |
| EP | 0944658 B1 | 6/2003 |
| EP | 1671624 | 6/2006 |
| EP | 1385452 B1 | 9/2006 |
| EP | 1409065 B1 | 1/2007 |
| EP | 1337284 B1 | 12/2007 |
| EP | 1911481 | 4/2008 |
| EP | 1521572 B1 | 3/2009 |
| WO | WO-88/04573 | 6/1988 |
| WO | WO-90/07545 | 7/1990 |
| WO | WO-95/28984 | 11/1995 |
| WO | WO-97/29850 | 8/1997 |
| WO | WO-98/25982 | 6/1998 |
| WO | WO-00/48660 | 8/2000 |
| WO | WO-01/26714 | 4/2001 |
| WO | WO-01/50943 | 7/2001 |
| WO | WO-03/077972 | 9/2003 |
| WO | WO-03/082188 | 10/2003 |
| WO | WO-2004/000267 | 12/2003 |
| WO | WO-2004/112653 | 12/2004 |
| WO | WO-2005/016401 | 2/2005 |
| WO | WO-2005/027906 | 3/2005 |
| WO | WO-2005/028006 | 3/2005 |
| WO | WO-2005/091922 | 10/2005 |
| WO | WO-2005/107705 | 11/2005 |
| WO | WO-2005/110362 | 11/2005 |
| WO | WO-2005/110436 | 11/2005 |
| WO | WO-2005/110473 | 11/2005 |
| WO | WO-2005/117780 | 12/2005 |
| WO | WO-2006/014484 | 2/2006 |
| WO | WO-2006/015385 | 2/2006 |
| WO | WO-2006/023530 | 3/2006 |
| WO | WO-2006/031358 | 3/2006 |
| WO | WO-2006/031388 | 3/2006 |
| WO | WO-2006/044614 | 4/2006 |
| WO | WO-2006/068838 | 6/2006 |
| WO | WO-2006/071554 | 7/2006 |
| WO | WO-2006/082588 | 8/2006 |
| WO | WO-2006/108054 | 10/2006 |
| WO | WO-2006/127962 | 11/2006 |
| WO | WO-2006125106 A1 | 11/2006 |
| WO | WO-2006/138609 | 12/2006 |
| WO | WO-2007/012974 | 2/2007 |
| WO | WO-2007035621 | 3/2007 |
| WO | WO-2007/038453 | 4/2007 |
| WO | WO-2007/044534 | 4/2007 |
| WO | WO-2007/047744 | 4/2007 |
| WO | WO-2007/066339 | 6/2007 |
| WO | WO-2007/084582 | 7/2007 |
| WO | WO-2007/084765 | 7/2007 |
| WO | WO-2007/101204 | 9/2007 |
| WO | WO-2007/117394 | 10/2007 |
| WO | WO-2007/131050 | 11/2007 |
| WO | WO-2007/133761 | 11/2007 |
| WO | WO-2007/133762 | 11/2007 |
| WO | WO-2008/003043 | 1/2008 |
| WO | WO-2008/005240 | 1/2008 |
| WO | WO-2008/011125 | 1/2008 |
| WO | WO-2008/033924 | 3/2008 |
| WO | WO-2008/040062 | 4/2008 |
| WO | WO-2008/045272 | 4/2008 |
| WO | WO-2008/052145 | 5/2008 |
| WO | WO-2008/060359 | 5/2008 |
| WO | WO-2008/061043 A2 | 5/2008 |
| WO | WO-2008/076544 | 6/2008 |
| WO | WO-2008/094989 | 8/2008 |
| WO | WO-2008/115290 | 9/2008 |
| WO | WO-2008/116165 | 9/2008 |
| WO | WO-2008/144340 | 11/2008 |
| WO | WO-2008/144919 | 12/2008 |
| WO | WO-2009/012075 | 1/2009 |
| WO | WO-2009/023615 | 2/2009 |
| WO | WO-2009/046164 | 4/2009 |
| WO | WO-2009/055620 | 4/2009 |
| WO | WO-2009/055671 | 4/2009 |

(56) References Cited

FOREIGN PATENT DOCUMENTS

| WO | WO-2009/055729 | 4/2009 |
|---|---|---|
| WO | WO-2009/055824 | 4/2009 |
| WO | WO-2009/061607 | 5/2009 |
| WO | WO-2009/073192 | 6/2009 |
| WO | WO-2009/086112 | 7/2009 |
| WO | WO-2009/089409 | 7/2009 |
| WO | WO-2009/094466 | 7/2009 |
| WO | WO-2009/112878 | 9/2009 |
| WO | WO-2009/117112 | 9/2009 |
| WO | WO-2009/124096 | 10/2009 |
| WO | WO-2009/128932 | 10/2009 |
| WO | WO-2009/134929 | 11/2009 |
| WO | WO-2009/137777 | 11/2009 |
| WO | WO-2010/008424 | 1/2010 |
| WO | WO-2010/021993 | 2/2010 |
| WO | WO-2010/047753 | 4/2010 |
| WO | WO-2010/062628 | 6/2010 |
| WO | WO-2010/066714 | 6/2010 |
| WO | WO-2010/075565 | 7/2010 |
| WO | WO-2010/078063 | 7/2010 |
| WO | WO-2010080987 A2 | 7/2010 |
| WO | WO-2010/088548 | 8/2010 |
| WO | WO-2010/093945 | 8/2010 |
| WO | WO-2010/095940 | 8/2010 |
| WO | WO-2010/125416 | 11/2010 |
| WO | WO-2010/126908 | 11/2010 |
| WO | WO-2010/135369 | 11/2010 |
| WO | WO-2010/141729 | 12/2010 |
| WO | WO-2010/147661 | 12/2010 |
| WO | WO-2011/008896 | 1/2011 |
| WO | WO-2011/008897 | 1/2011 |
| WO | WO-2011/028850 | 3/2011 |
| WO | WO-2011/034627 | 3/2011 |
| WO | WO-2011/079232 | 6/2011 |
| WO | WO-2012/019136 | 2/2012 |
| WO | WO-2013/082452 A1 | 6/2013 |
| WO | WO-2013/116061 A1 | 8/2013 |

OTHER PUBLICATIONS

Avery et al., "Intravitreal bevacizumab (Avastin) in the treatment of proliferative diabetic retinopathy," Ophthalmology. Oct. 2006, 113(10):1695-1705.e6.

Bakri et al., "The effect of intravitreal triamcinolone acetonide on intraocular pressure," Ophthalmic Surgery, Lasers and Imaging, Sep./Oct. 2003; 34(5): 386-390.

Bird et al., Transport Phenomena, John Wiley & Sons, Inc., New York, 1960, pp. 196-201.

Block et al., "Solubility and dissolution of triamcinolone acetonide," Journal of Pharmaceutical Sciences, Apr. 1973; 62(4):617-621.

Castro et al., "Effect of COX inhibitors on VEGF-induced retinal vascular leakage and experimental corneal and choroidal neovascularization," Exp Eye Res. Aug. 2004;79(2):275-285.

Chirila et al., "The Vitreous Humor" in Handbook of Biomaterial Properties, eds. Black & Hastings. Chapman & Hall, London, 1998; pp. 125-131.

Cousins et al., "Program # 1251—Targeting Complement Factor 5 in Combination with Vascular Endothelial Growth Factor (VEGF) Inhibition for Neovascular Age Related Macular Degeneration (AMD): Results of a Phase 1 Study," [Presentation Abstract], AMD Clinical Trials Session # 220, May 3, 2010.

Deissler et al., "VEGF-induced effects on proliferation, migration and tight junctions are restored by ranibizumab (Lucentis) in microvascular retinal endothelial cells," Br J Ophthalmol 2008;92:839-843.

Donoso et al., "The role of inflammation in the pathogenesis of age-related macular degeneration," Surv Ophthalmol. Mar.-Apr. 2006;51(2):137-52.

European Medicine Agency, Scientific Discussion; retrieved from the Internet; <http://www.ema.europa.eu/docs/en_GB/document_library/EPAR_-_Scientific_Discussion/human/000715/WC500043550.pdf>, EMEA 2007, 54 pages total. 2007.

Funatsu et al. "Association of vitreous inflammatory factors with diabetic macular edema." Ophthalmology 2009;116:73-79.

Gaudreault et al., "Preclinical Pharmacokinetics of Ranibizumab (rhuFabV2) after a Single Intravitreal Administration," Investigative Ophthalmology and Visual Science. 2005;46:726-733. Retrieved from the Internet: <<http://www.iovs.org/cgi/reprint/46/2/726>>.

Gillies et al., "Intravitreal triamcinolone for refractory diabetic macular edema: two-year results of a double-masked, placebo-controlled, randomized clinical trial," Ophthalmology. Sep. 2006;113(9):1533-1538.

Hastedt & Wright, "Diffusion in porous materials above the percolation threshold," Pharm. Res. Sep. 1990; 7(9):893-901 (1990).

Heier et al, "Ketorolac versus prednisolone versus combination therapy in the treatment of acute pseudophakic cystoid macular edema," Ophthalmology. Nov. 2000;107(11):2034-2038;discussion 2039.

Jena et al., "A Novel Technique for Surface Area and Particle Size Determination of Components of Fuel Cells and Batteries," Porous Materials, Inc., Dec. 2006, 3 pages total. Downloaded from the Internet: <<http://www.pmiapp.com/publications/docs/A_Novel_technique_for_surface area.pdf>>.

Kang et al., "Inhibitory effects of anti-inflammatory drugs on interleukin-6 bioactivity," Biol Pharm Bull. Jun. 2001;24(6):701-703.

Lopez-Armada et al., "Modulation of cell recruitment by anti-inflammatory agents in antigen-induced arthritis," Ann Rheum Dis Nov. 2002;61(11):1027-1030.

Luncentis, INN-Ranibizumab, "Scientific Discussion," European Medicines Agency; retrieved from the Internet:<http://www.ema.europa.eu/docs/en_GB/document_library/EPAR_-Assessment_Report_-_Variation/human/000715/WC500101009.pdf>. Oct. 21, 2010.

Metal Powder Industries Federation, Porous Metal Design Guidebook, 2007, 24 pages total. Downloaded from the Internet: <<http://www.mpif.org/DesignCenter/porous.pdf>>.

MOTT Corporation, "Sintered Metal Powder Media," American Filtration & Separation Society 2007, 2 pages total. Downloaded from the Internet:<<http://www.afssociety.org/education/0907oneminute.htm>>.

Navarro, "The Optical Design of the Human Eye: a Critical Review," J Optom, Jan.-Mar. 2009 2(1): 3-18.

Okabe et al., "Intraocular tissue distribution of betamethasone after intrascleral administration using a non-biodegradable sustained drug delivery device," Investigative Ophthalmology and Visual Science. 2003;44:2702-2707. Downloaded from the Internet: <<http://www.iovs.org/cgi/reprint/44/6/2702>>.

Rosenfeld, "The Latest Research: Intravitreal Bevacizumab for Proliferative Diabetic Retinopathy," Review of Ophthalmology's Retina Online, Feb. 2006; retrieved from the Internet: http://www.revophth.com/archive/newsletter/0206_retina.htm.

Smith et al., "Spectrophotometric determination of pKa values for fluorescein using activity coefficient corrections," WaterSA 2002; 28(4):395-402.

Soheilian et al., "Pilot Study of Intravitreal Injection of Diclofenac for Treatment of Macular Edema of Various Etiologies," Retina, Mar. 2010; 30(3): 509-515.

Theodossiadis et al., "Intravitreal administration of the anti-tumor necrosis factor agent infliximab for neovascular age-related macular degeneration," Am J Ophthalmol. May 2009;147(5):825-830.

Williams et al., "Treating Diabetic Macular Edema With Ocular NSAIDs," Retinal Physician, Nov. 2007; retrieved from the Internet Nov. 11, 2007. http://www.retinalphysician.com/article.aspx?article=101096>, 5 pages total.

Edelhauser, H et al. "Ophthalmic Drug Delivery Systems for the Treatment of Retinal Diseases Basic Research to Clinical Applications." Investigative Ophthalmology & Visual Science, Nov. 2010. vol. 51, No. 11. pp. 5403-5420.

(56) References Cited

OTHER PUBLICATIONS

International Search Report dated Jun. 18, 2013, for PCT application No. PCT/US2013/022770.

* cited by examiner

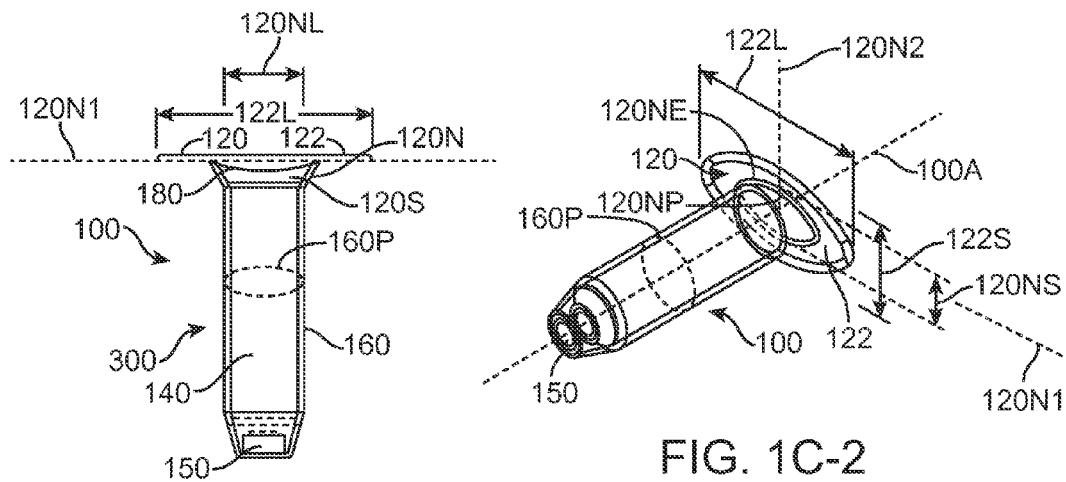
FIG. 1C-1
FIG. 1C-2
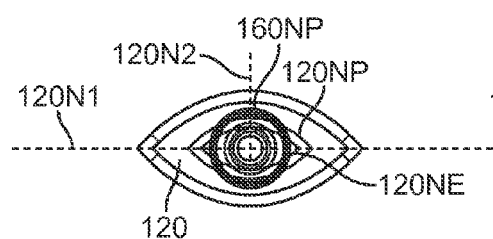
FIG. 1C-3
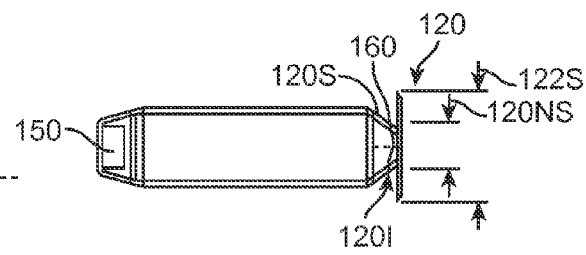
FIG. 1C-4
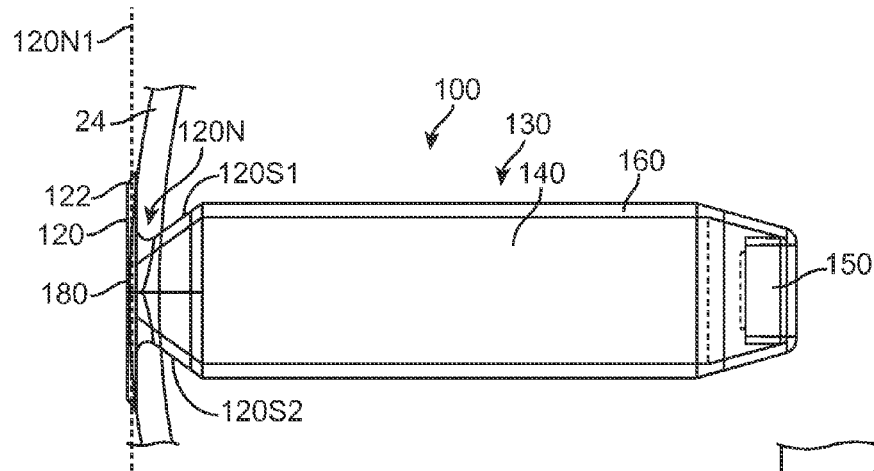
FIG. 1C-5
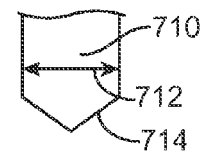
FIG. 1C-6

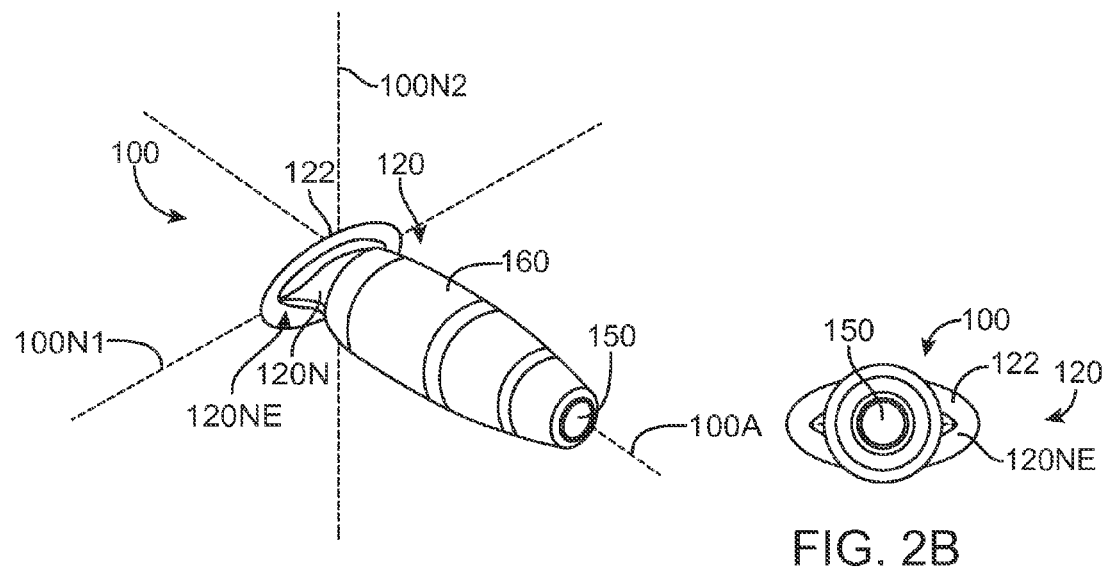
FIG. 2A
FIG. 2B
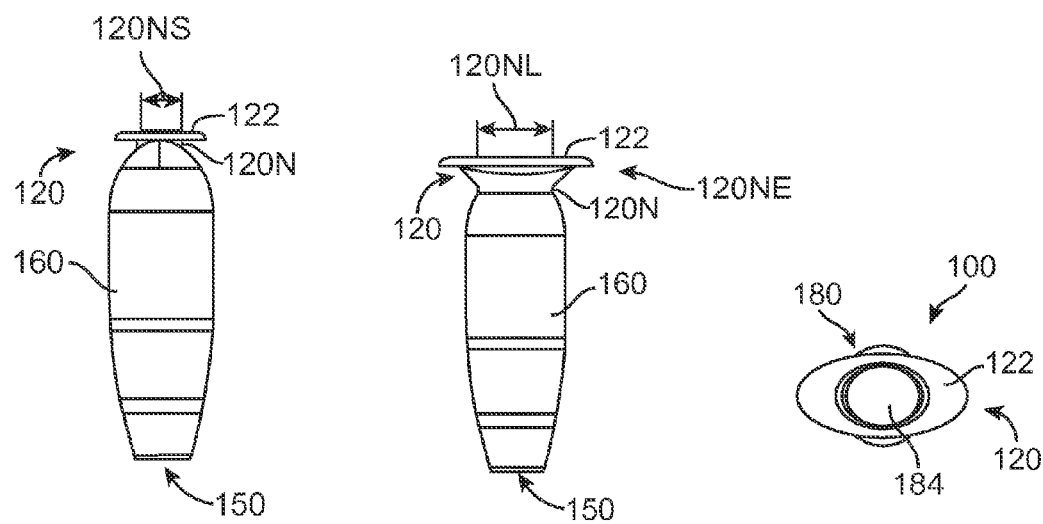
FIG. 2C1
FIG. 2C2
FIG. 2D

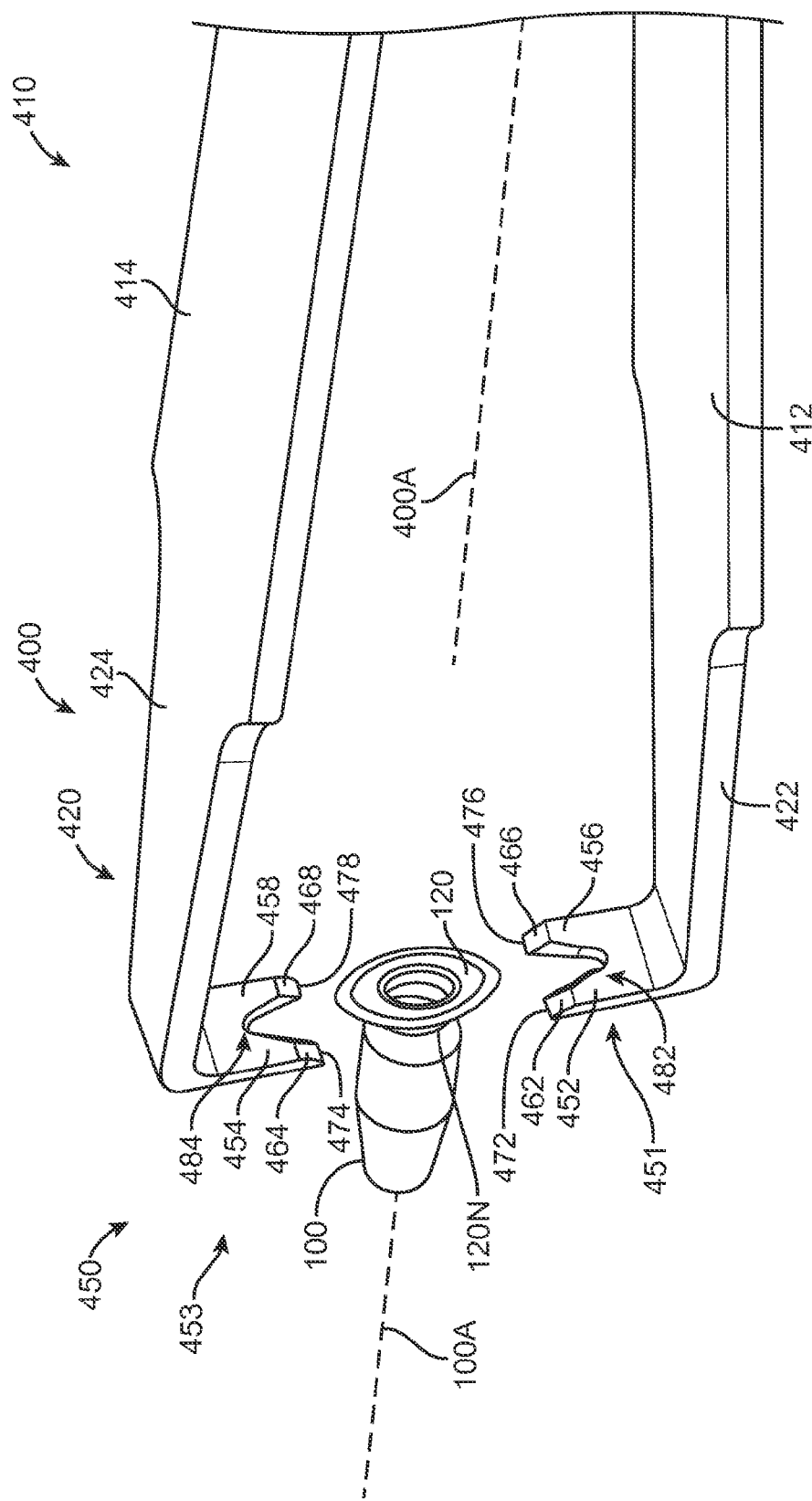

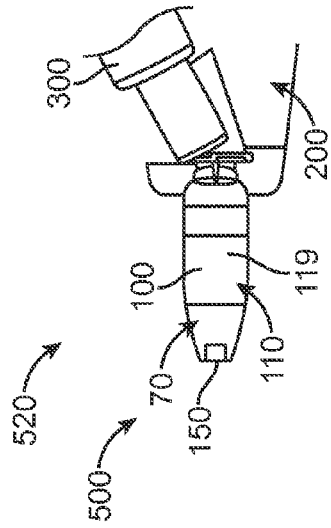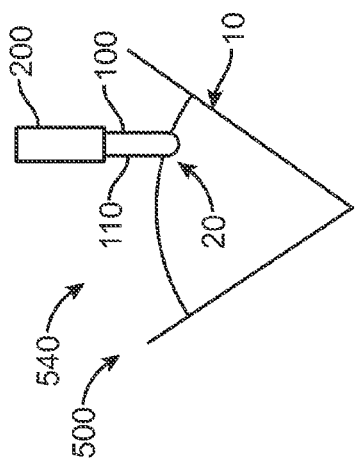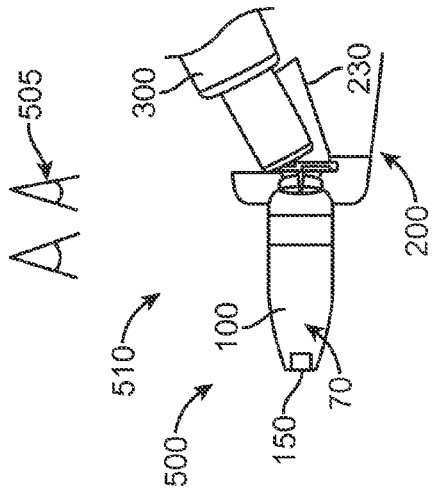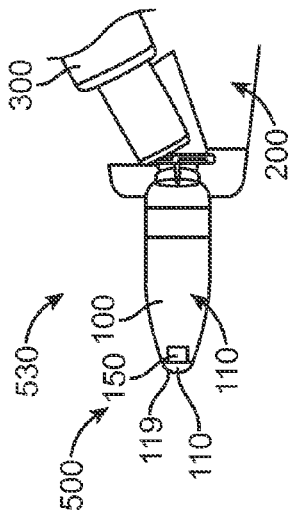

INSERTION AND REMOVAL METHODS AND APPARATUS FOR THERAPEUTIC DEVICES

CROSS-REFERENCE TO RELATED APPLICATION

This application is a national stage application, filed under 35 U.S.C. § 371, of PCT Application No. PCT/US2013/022770, filed on Jan. 23, 2013, which claims priority to U.S. Provisional Application No. 61/594,961 filed on Feb. 3, 2012, the contents of which are incorporated herein by reference in their entirety for all purposes.

BACKGROUND

The present disclosure is generally related to methods and apparatus to insert and remove implantable devices. Although specific reference is made to placement in the eye, embodiments as described herein can be used with many implantable devices in locations away from the eye, such as orthopedic, intraluminal and transdermal locations.

Implantable devices can be used to provide a therapeutic agent to one or more locations of a patient. The implantable device may have a reservoir of therapeutic agent, and a structure to retain the implantable device at a desired location of the patient. The implantable device may have a chamber for storing the therapeutic agent, and the agent can be released into the patient to provide a therapeutic benefit. After an amount of time, the amount of fluid released can be less than ideal, and the fluid of the implantable device may be replaced, refilled, or exchanged to provide additional amounts of therapeutic agent to extend the therapy.

The prior methods and apparatus to place an implantable device in the body can be less than ideal in at least some instances. For example, the amount of therapeutic fluid placed in an implanted therapeutic device with injection can be less than ideal in at least some instances. At least some of the prior devices implanted in the eye can be small to decrease interference with vision, and the refill port of such devices can be difficult to fill in at least some instances. The eye can move, and alignment and placement of the implantable device in the eye can be more difficult than would be ideal in at least some instances.

In light of the above, it would be desirable to provide improved treatments for the eye and improved methods and apparatus to place implantable devices in the eye and to place therapeutic fluids in the implantable devices. Ideally, these treatments, methods and apparatus would decrease at least some of the deficiencies of the prior methods and apparatus, and would provide improved placement and removal of devices implanted within the eye.

SUMMARY

Embodiments of the present disclosure provide improved methods and apparatus to insert and remove an implantable device to treat a patient. In many embodiments, the methods and apparatus can provide injection of a therapeutic agent into an implantable device prior to insertion. The implantable device can be manufactured and provided to a clinic without a therapeutic agent, such that the therapeutic agent can be placed in the implantable device in the clinic prior to insertion.

In a first aspect, described herein is an apparatus to insert an implantable therapeutic device into a patient. The apparatus includes a proximal handle, and a distal placement portion coupled to the proximal handle and configured to hold the implantable therapeutic device. The distal placement portion includes a first side having a first engagement structure at a distal end of the first side, the first engagement structure configured to surround at least a first portion of a proximal end region of the implantable therapeutic device. The distal placement portion includes a second, opposite side having a second engagement structure at a distal end of the second side, the second engagement structure configured to surround at least a second, opposite portion of the proximal end region of the implantable therapeutic device.

The apparatus can further include the implantable therapeutic device. The implantable therapeutic device can include a retention structure at the proximal end region having a narrow portion, a shoulder and a proximal extension. Each of the first and second engagement structures can include a protrusion having a surface contour shaped and sized to engage a portion of the retention structure. Each of the protrusions can be configured to extend into the narrow portion. The protrusions can extend into the narrow portion, a proximal surface of each protrusion can engage a distal surface of the proximal extension and a distal surface of each protrusion can engage the shoulder.

The distal placement portion can further include a recess through which a proximal surface of the proximal extension is accessible. The distal placement portion can further include a guide having at least one guide surface configured to support and maintain alignment of a needle extending at an angle oblique to a longitudinal axis of the implantable device prior to penetration of the implantable device by the needle. The needle can include a connector and wherein the at least one guide surface has a shape complimentary to the connector to receive the connector and maintain alignment of the needle relative to the implantable device. The proximal handle can include first and second opposing handles extending on opposite sides of a longitudinal axis. The first opposing handle can be coupled to a proximal end of the first side and the second opposing handle can be coupled to a proximal end of the second side. The first and second opposing handles can be configured to urge the first side and the second side toward each other to engage the implantable device when the first and second opposing handles move away from the axis and to urge the first side and the second side away from each other to release the implantable device when the first and second opposing handles move toward the axis. The first and second opposing handles can be configured to urge the first side and the second side toward each other to engage the implantable device when the first and second opposing handles move toward the axis and to urge the first side and the second side away from each other to release the implantable device when the first and second opposing handles move away from the axis.

In an interrelated aspect, disclosed herein is a method of treating a patient including holding with an insertion apparatus an implantable device having an axis and a penetrable barrier, such that the axis of the implantable device and an axis of the insertion apparatus are concentric. The method includes advancing a needle through the penetrable barrier at an angle oblique to the concentric axes. The method includes injecting a therapeutic fluid through the needle advanced through the penetrable barrier and into a reservoir chamber of the implantable device. The method includes implanting the implantable device into an incision in a tissue of the patient.

The axis of the implantable device and the axis of the insertion apparatus can be concentric when the therapeutic fluid is injected into the reservoir chamber of the implantable device.

In an interrelated aspect disclosed herein is a kit to treat a patient including an insertion apparatus of any of those described herein, an implantable therapeutic device, and packaging to contain the insertion apparatus and the implantable therapeutic device.

Additional aspects are recited in the claims below, and can provide additional summary in accordance with embodiments as described herein. It is contemplated that the embodiments as described herein and recited in the claims may be combined in many ways, and any one or more of the elements recited in the claims can be combined together in accordance with embodiments and teachings as described herein.

BRIEF DESCRIPTION OF THE DRAWINGS

FIG. 1C-1 shows a side cross-sectional view of a therapeutic device including a retention structure having a cross-section sized to fit in an elongate incision, in accordance with embodiments;

FIG. 1C-2 shows an isometric view of the therapeutic device as in FIG. 1C-1;

FIG. 1C-3 shows a top view of the therapeutic device as in FIG. 1C-1;

FIG. 1C-4 shows a side cross sectional view along the short side of the retention structure of the therapeutic device as in FIG. 1C-1;

FIG. 1C-5 shows a side view of the therapeutic device as in FIG. 1C-1 implanted in the sclera;

FIG. 1C-6 shows a cutting tool including a blade having a width corresponding to the perimeter of the barrier and the perimeter of the narrow retention structure portion, in accordance with embodiments;

FIG. 2A shows an isometric view of the therapeutic device having a retention structure with an elongate cross-sectional size, in accordance with embodiments;

FIG. 2B shows a distal end view of the therapeutic device as in FIG. 2A;

FIG. 2C1 shows a side view of the short axis of the narrow neck portion of the therapeutic device as in FIG. 2A;

FIG. 2C2 shows a side view of the long axis of the narrow neck portion of the therapeutic device as in FIG. 2A;

FIG. 2D shows a proximal view of the therapeutic device as in FIGS. 2A;

FIG. 4B shows the removal tool of FIG. 4A aligned with an implantable device, in accordance with embodiments;

FIG. 5A shows a needle inserted into an air-filled implantable device, in accordance with embodiments;

FIG. 5B shows a therapeutic fluid placed in the implantable device of FIG. 5A, in accordance with embodiments;

FIG. 5C shows the therapeutic fluid injected into an implantable device and seeping through a porous structure on the distal end of the device of FIG. 5A, in accordance with embodiments;

FIG. 5D shows the implantable device being placed in the eye, in accordance with embodiments;

DETAILED DESCRIPTION

Figure 1A:
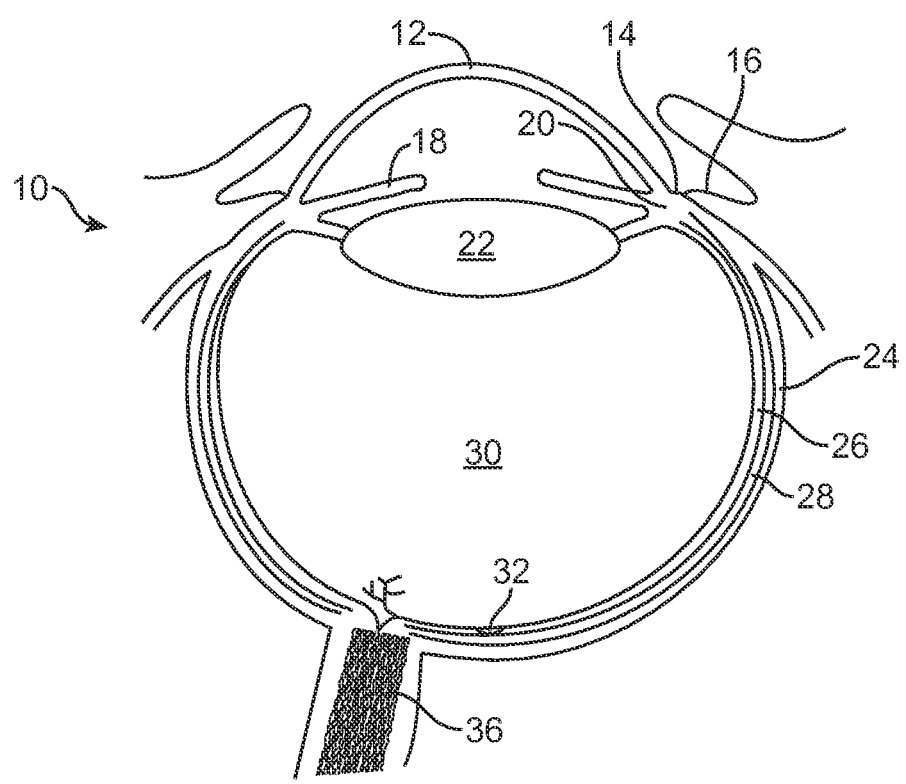
FIG. 1A shows an eye suitable for incorporation of the therapeutic device, in accordance with embodiments.

Embodiments as described herein can be combined in many ways to treat one or more diseases of a patient such as a disease of the eye. The embodiments as described herein are well suited to treat patients with a therapeutic agent for an extended time, such as may be provided with an implantable device. Although specific reference is made to ophthalmic treatment of the eye, the methods and apparatus to place and remove an implantable device can be used with many implantable devices and treatments of one or more of many diseases, such as systemic medication to treat systemic disease, orthopedic treatment to treat orthopedic disorders, or dental treatment, for example. The insertion and removal apparatus and methods as described herein are well suited for use with many drug delivery devices, such as refillable diffusion based devices, and can be exceptionally well suited for diffusion devices having a porous drug release structure configured for extended release in which the porous structure inhibits flow of fluid during exchange. The insertion and removal apparatus and methods as describe herein are well suited for diagnoses and treatment of the eye, for example with diagnosis and treatment of the eye based on the implantable device fluid received with the exchange apparatus with the fluid is injected. The methods and apparatus as described herein are well suited for combination with implantable devices and injector apparatus as described in U.S. patent application Ser. No. 12/696,678, filed on Jan. 29, 2010, entitled "Posterior Segment Drug Delivery", Publication No. 2010/0255061; and U.S. PCT Pat. App. No. PCT/US2011/046812, filed Aug. 5, 2011, entitled "Injector Apparatus and Method for Drug Delivery", the entire disclosures of which are incorporated herein by reference.

As used herein like numerals and/or letters denote like elements in the drawings and text as will be apparent to a person of ordinary skill in the art.

FIG. 1A shows an eye 10 suitable for placement of the therapeutic device. The eye has a cornea 12 and a lens 22 configured to form an image on the retina 26. The cornea can extend to a limbus 14 of the eye, and the limbus can connect to a sclera 24 of the eye. A conjunctiva 16 of the eye can be disposed over the sclera 24. The lens 22 can accommodate to focus on an object seen by the patient. The eye has an iris 18 that may expand and contract in response to light. The eye also includes a choroid 28 disposed the between the sclera 24 and the retina 26. The retina includes the macula 32. The eye includes a pars plana 20, which is an example of a region of the eye suitable for placement and retention, for example anchoring, of the therapeutic device 100 as described herein and shown in 1B. The pars plana region 20 may include sclera 24 and conjunctiva 16 disposed between the retina 26 and cornea 12. The therapeutic device can be positioned so as to extend from the pars plana region 20 into the vitreous humor 30 to release the therapeutic agent. The therapeutic agent can be released into the vitreous humor 30, such that the therapeutic agent arrives at the retina 26 and choroids 28 for therapeutic effect on the macula 32. The vitreous humor of the eye 30 includes a liquid disposed between the lens 22 and the retina 26. The vitreous humor 30 may include convection currents to deliver the therapeutic agent to the macula 32.

Figure 1B:
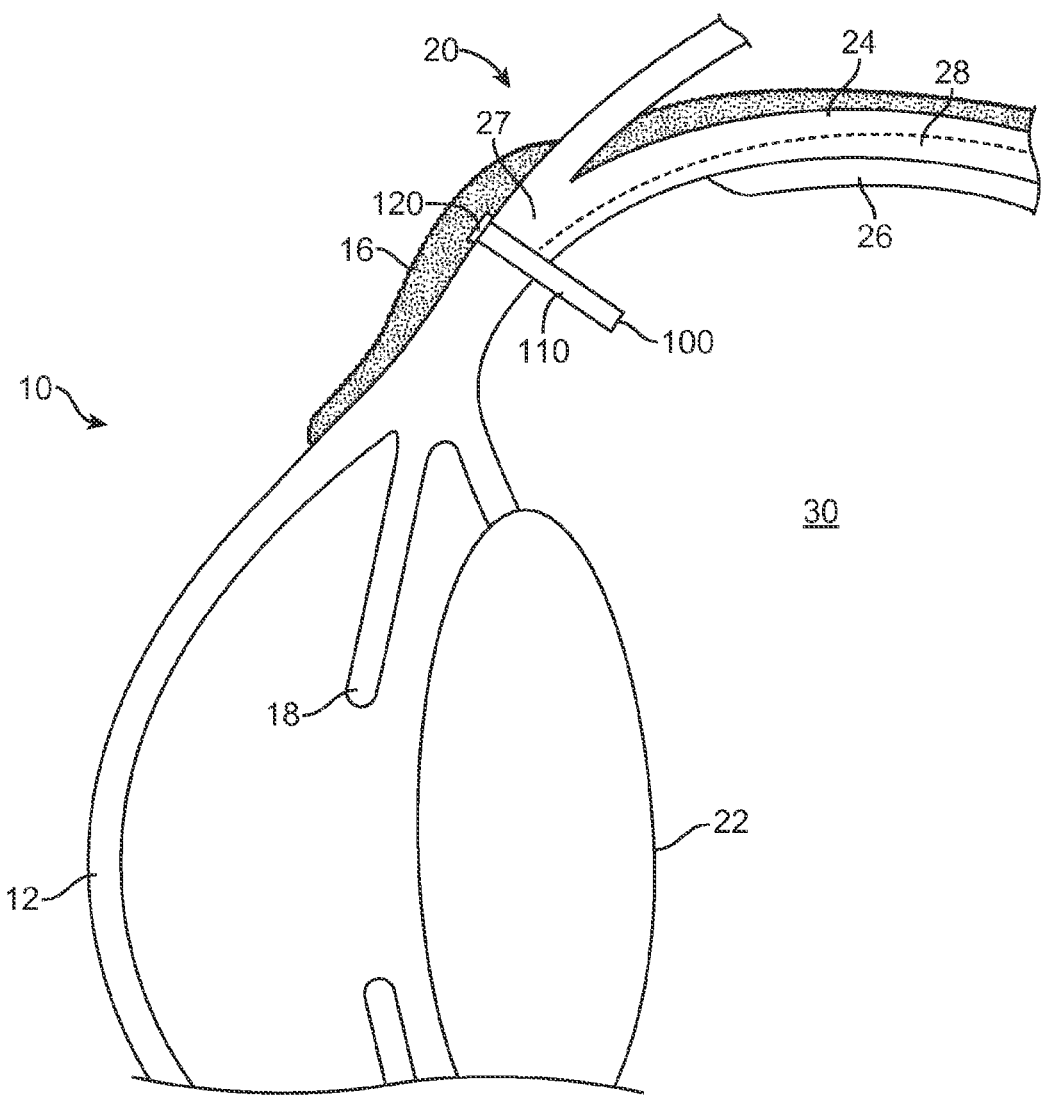
FIG. 1B shows a therapeutic device implanted under the conjunctiva and extending through the sclera to release a therapeutic agent into vitreous humor of the eye so as to treat the retina of the eye, in accordance with embodiments.

FIG. 1B shows a therapeutic device 100 implanted under the conjunctiva 16 and extending through the sclera 24 to release a therapeutic agent 110 into vitreous humor 30 of the eye 10 so as to treat the retina 26 of the eye. The therapeutic device 100 can include a retention structure 120 such as a smooth protrusion configured for placement along the sclera 24 and under the conjunctiva 16, such that the conjunctiva 16 can cover the therapeutic device and protect the therapeutic device 100. When the therapeutic agent 110 is inserted into the device 100, the conjunctiva 16 may be lifted away, incised, or punctured with a needle to access the therapeutic device 100. The eye 10 can include an insertion of the tendon 27 of the superior rectus muscle to couple the sclera 24 of the eye to the superior rectus muscle. The device 100 may be positioned in many locations of the pars plana region 20, for example away from tendon 27 and one or more of posterior to the tendon, posterior to the tendon, under the tendon, or with nasal or temporal placement of the therapeutic device.

While the implant can be positioned in the eye in many ways, work in relation to embodiments suggests that placement in the pars plana region can release therapeutic agent into the vitreous to treat the retina, for example therapeutic agent including an active ingredient composed of large molecules.

Therapeutic agents 110 suitable for use with device 100 include one or more of many therapeutic agents, for example as listed in Table 1A, herein below. The therapeutic agent 110 of device 100 can include one or more of an active ingredient of the therapeutic agent, a formulation of the therapeutic agent, a commercially available formulation of the therapeutic agent, a physician prepared formulation of therapeutic agent, a pharmacist prepared formulation of the therapeutic agent, or a commercially available formulation of therapeutic agent having an excipient. The therapeutic agent may be referred to with generic name or a trade name, for example as shown in Table 1A.

The therapeutic device 100 can be implanted in the eye to treat the eye for as long as is helpful and beneficial to the patient. For example the device can be implanted for at least about 5 years, such as permanently for the life of the patient. Alternatively or in combination, the device can be removed when no longer helpful or beneficial for treatment of the patient.

FIG. 1C-1 shows a side cross-sectional view of therapeutic device 100 including a retention structure 120 having a cross-section sized to fit in an elongate incision. The cross-section sized to fit in the elongate incision can include a narrow portion 120N of retention structure 120 that is sized smaller than the extension 122. The narrow portion 120N (shown in FIG. 1C-2) sized to fit in the elongate incision can include an elongate cross section 120NE sized to fit in the incision. The narrow portion 120N can include a cross-section having a first cross-sectional long distance 120NL, or first dimensional width, and a second cross-sectional short distance 120NS (shown in FIG. 1C-2), or second dimensional width, in which the first cross-sectional distance across is greater than the second cross-sectional distance across such that the narrow portion 120N includes an elongate cross-sectional profile. The first cross-sectional long distance 120NL may extend along a first axis 120N1 and the second cross-sectional short distance 120NS may extend along a second axis 120N2 (shown in FIG. 1C-2).

In many embodiments, the retention structure 120 includes a shoulder 120S extending from the narrow portion 120N to the wall of the reservoir chamber 140, which can include a rigid or expandable annular wall. The shoulder portion 120S can extend from the narrow portion so as to engage the sclera opposite extension 122 and hold the device 100 in the pars plana region. The shoulder 120S of retention structure 120 can include a first shoulder 120S1 on a first side of the retention structure and a second shoulder 120S2 on a second side of the retention structure with axis 120N1 extending therebetween (as shown in 1C-5). Alternatively, the retention structure 120 can include a rotationally symmetric narrow portion 120N having a first side and a second side to fit a dilated incision of the eye, for example, and shoulder 120S can include a rotationally symmetric shoulder extending from the narrow portion 120N to engage a lower portion of the sclera.

The elongate cross section 120NE, shown in FIGS. 1C-2 and 1C-3, of the narrow portion 120N can be sized in many ways to fit the incision. The elongate cross section 120NE having long distance 120NL and short distance 120NS and can include one or more of many shapes such as dilated slit, dilated slot, lentoid, oval, ovoid, or elliptical. The dilated slit shape and dilated slot shape may correspond to the shape sclera tissue assumes when cut and dilated. The lentoid shape may correspond to a biconvex lens shape. The elongate cross-section of the narrow portion can include a first curve along a first axis and a second curve along a second axis different than the first curve.

The porous structure 150 can be located on a distal end portion of the therapeutic device, and the retention structure 120 can be located on a proximal portion of therapeutic device 100, as shown in FIGS. 1C-1, 1C-2, 1C-4, and 1C-5. The porous structure 150 can include one or more of many porous structures such as a sintered material, openings in a non-permeable material, openings having a size and number to release therapeutic agent at an intended rate, a plurality of holes etched in a material, a semi-permeable membrane, or nano-channels, for example.

The reservoir 130 can be configured in many ways, and can include a rigid walled reservoir, for example, or an expandable reservoir. The barrier 160 may define a size of reservoir 130. The barrier 160 and reservoir 130 may each include a circular, an elliptical, oval or other cross-sectional size, for example.

FIG. 1C-2 shows an isometric view of the therapeutic device as in FIG. 1C-1.

FIG. 1C-3 shows a top view of the therapeutic device as in FIG. 1C-1.

FIG. 1C-4 shows a side cross sectional view along the short side of the retention structure of the therapeutic device as in FIG. 1C-1.

FIG. 1C-5 shows a side view of the therapeutic device as in FIG. 1C-1 implanted in the sclera.

FIG. 1C-6 shows a cutting tool 710 including a blade 714 having a width 712 corresponding to perimeter 160P (shown in FIGS. 1C-1, 1C-2, and 1C-3) of the barrier 160 and the perimeter 120NP of the narrow portion. The cutting tool can be sized to the narrow portion 120N so as to seal substantially the incision with the narrow portion when the narrow portion is positioned against the sclera. For example, the width 712 can be about one half of the perimeter 160P of the barrier 160 and about one half of the perimeter 120NP of the narrow portion 120N. For example, the outside diameter of the tube of barrier 160 can be about 3 mm such that the perimeter of 160P is about 6 mm, and the narrow portion perimeter 120NP is about 6 mm. The width 712 of the blade 710 can be about 3 mm such that the incision includes an opening having a perimeter of about 6 mm so as to seal the incision with the narrow portion 120N. Alternatively, perimeter 160P of barrier 160 may have a size slightly larger than the incision and the perimeter of the narrow portion.

The retention structure includes narrow portion 120N having short distance 120NS and long distance 120NL so as to fit in an elongate incision along the pars plana of the eye. The retention structure includes extension 122, and the extension 122 of the retention structure 120 can include a short distance across 122S and a long distance across 122L, aligned with the short distance 120NS and long distance 120NL of the narrow portion 120N of the retention structure 120. The narrow portion 120 can include an indentation 120I sized to receive the sclera, and the indention 120I can include an indentation relative to a maximum dimension across the reservoir chamber 140 and the extension 122 such that the sclera is retained with the indentation 120I. The indentation 120I can include a portion of the extension 122, a portion of the shoulder 120S and a portion of the retention structure extending therebetween, for example.

The therapeutic device 100 can include a non-circular cross-sectional size, and the reservoir chamber 140 can include a rigid walled reservoir having a non-circular, for example elliptical or lentoid cross-sectional size.

FIG. 2A shows an isometric view of the therapeutic device having a retention structure including a narrow portion 120N with an elongate cross-sectional size 120NE.

FIG. 2B shows a distal end view of the therapeutic device as in FIG. 2A.

FIG. 2C1 shows a side view of the short distance 120NS of the narrow portion 120N of the therapeutic device as in FIG. 2A.

FIG. 2C2 shows a side view of the long distance 120NL of the narrow portion 120N of the therapeutic device 100 as in FIG. 2A.

FIG. 2D shows a proximal view of the therapeutic device as in FIG. 2A.

Figure 2E:
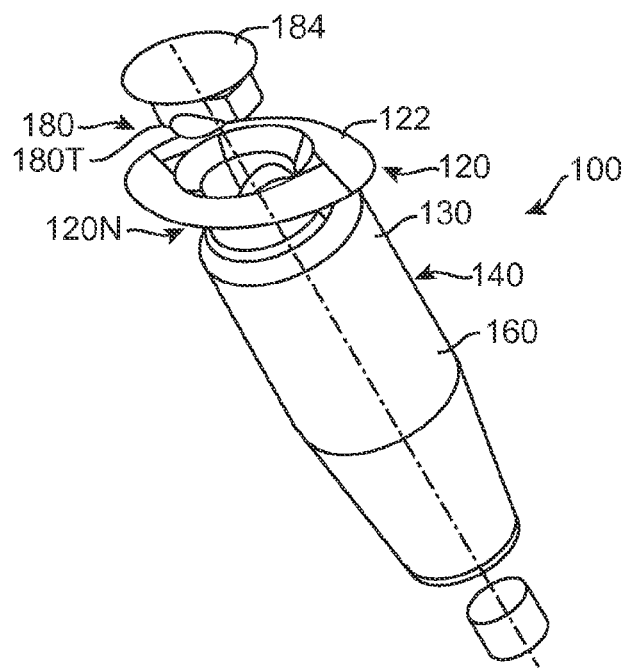
FIGS. 2E to 2G show exploded assembly drawings for the therapeutic device as in FIGS. 2A to 2D.
Figure 2F:
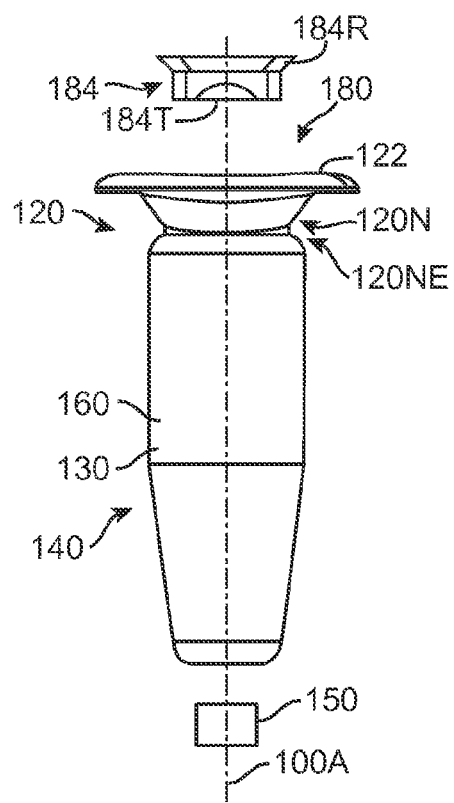
Figure 2G:
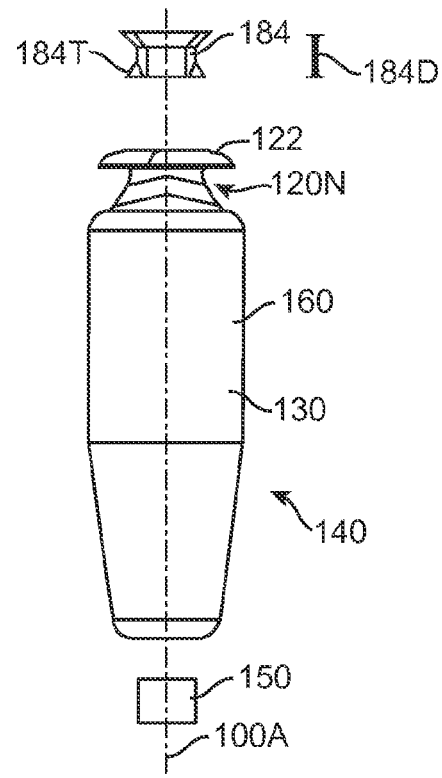

FIGS. 2E to 2G show exploded assembly drawings for the therapeutic device 100 as in FIGS. 2A to 2D. The assembly drawings show isometric and thin side profiles views of the elongate portion 120NE of the narrow portion of the retention structure 120N. The therapeutic device 100 has an elongate axis 100A.

The penetrable barrier 184, for example the septum, can be inserted into the access port 180. The penetrable barrier can include an elastic material sized such that the penetrable barrier can be inserted into the access port 180. The implantable device can include penetrable barrier 184 having a first outer and a second inner surface and a thickness extending a distance 184D between the first surface and the second surface. The penetrable barrier can include one or more elastic materials such as siloxane or rubber. The penetrable barrier can include tabs 184T to retain the penetrable barrier in the access port. The penetrable barrier 184 can include a beveled upper rim 184R sized to seal the access port 180. The access port 180 of the reservoir container 130 can include a beveled upper surface to engage the beveled rim and seal the penetrable barrier against the access port 180 when the tabs 184T engage an inner annular or elongate channel of the access port. The penetrable barrier 184 can include an opaque material, for example a grey material, for example silicone, such that the penetrable barrier can be visualized by the patient and treating physician.

The reservoir container 130 of the device can include a rigid biocompatible material that extends at least from the retention structure to the rigid porous structure, such that the reservoir includes a substantially constant volume when the therapeutic agent is released with the rigid porous structure so as to maintain a stable release rate profile, for example when the patient moves. Alternatively or in combination, the reservoir container 130 can include an optically transmissive material such that the reservoir container 130 can be translucent, for example transparent, such that the chamber of reservoir 140 can be visualized when the device is loaded with therapeutic agent outside the patient prior to implantation, for example when injected with a formulation of therapeutic agent prior to implantation in the physician's office. This visualization of the reservoir 140 can be helpful to ensure that the reservoir 140 is properly filled with therapeutic agent by the treating physician or assistant prior to implantation. The reservoir container can include one or more of many biocompatible materials such as acrylates, polymethylmethacrylate, siloxanes, metals, titanium stainless steel, polycarbonate, polyetheretherketone (PEEK), polyethylene, polyethylene terephthalate (PET), polyimide, polyamide-imide, polypropylene, polysulfone, polyurethane, polyvinylidene fluoride or PTFE. The biocompatible material of the reservoir container can include an optically transmissive material such as one or more of acrylate, polyacrylate, methlymethacraylate, polymethlymethacrylate (PMMA), polyacarbonate or siloxane. The reservoir container 130 can be machined from a piece of material, or injection molded, so as to form the retention structure 120 including extension 122 and the elongate narrow portion 120NE. The extension 122 can include a translucent material such that the physician can visualize tissue under the flange to assess the patient and to decrease appearance of the device 100 when implanted. The reservoir container 130 can include a channel extending along axis 100A from the access port 180 to porous structure 150, such that formulation injected into device 100 can be released in accordance with the volume of the reservoir and release rate of the porous structure 150 as described herein. The porous structure 150 can be affixed to the distal end of therapeutic device 100, for example with glue. Alternatively or in combination, the distal end of the reservoir container 130 can include an inner diameter sized to receive the porous structure 150, and the reservoir container 130 can include a stop to position the porous structure 150 at a predetermined location on the distal end so as to define a predetermined size of reservoir 140.

Figure 3A:
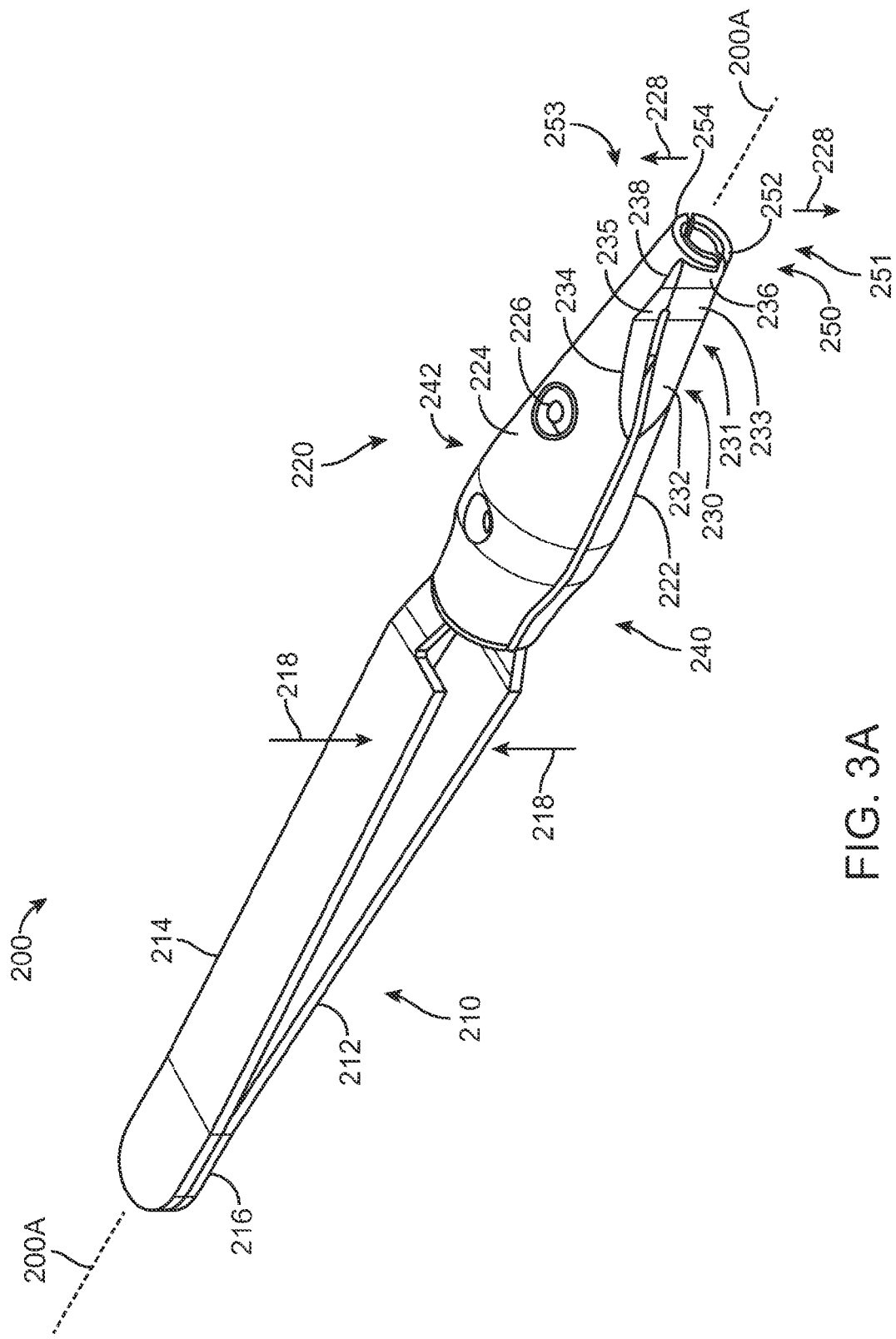
FIG. 3A shows an insertion apparatus in accordance with embodiments.

FIG. 3A shows an insertion apparatus 200. The insertion apparatus includes a proximal handle 210 and a distal placement portion 220. The handle 210 includes a first extension 212 and a second extension 214. A proximal end portion 216 couples the first extension 212 to the second extension 214. The insertion apparatus 200 includes an axis 200A extending along an elongate dimension of the insertion apparatus 200.

The proximal handle 210 includes structures to manipulate the distal placement portion 220. The first extension 212 and second extension 214 may be combined in many ways to manipulate the distal placement portion 220. The first extension 212 and the second extension 214 may extend to opposing sides of the distal portion 220. The first extension 212 and the second extension 214 and can include a resilient spring having the extensions coupled together at the distal end portion 216, for example with a weld on the distal end portion 216. The user can urge the first extension 212 toward the second extension 214 against the resilient extensions as shown with arrows 218, and the user can release the extensions, such that the spring forces urges the first extension 212 away from the second extension 214 opposite arrows 218.

The distal placement portion 220 includes structures to hold and place the implantable device 100. The distal placement portion 220 includes a guide 230 and an engagement structure 250. The engagement structure 250 is configured to engage the implantable device 100, and the guide 230 is configured to facilitate alignment and access to the implantable device 100 with a needle or other filling device so as to place therapeutic agent inside the implantable device 100. The guide 230 can be located on a front 240 of the placement portion 220, and can be readily viewed by a user. The front 240 is located opposite a back 242. The guide 230 located on the front 240 allows viewing of the recess 231 when the needle is advanced into the recess, as will be described in more detail below. The distal placement portion 220 includes a first side 222 and a second side 224 located opposite the first side 222. The first side 222 is movable opposite the second side 224 so as to engage the implantable device 100 with the first side 222 and the second side 224.

The engagement structure 250 can be configured to contact the implantable device in many ways, and can include a first engagement structure 251 on first side 222 and a second engagement structure 253 on the second side 224 opposite the first engagement structure. The first engagement structure 251 on first side 222 includes a first projection 252 extending at least partially around axis 200A. The second engagement structure 252 on second side 224 includes a second projection 254 extending at least partially around axis 200A opposite the first projection 252. The first and second projections 252, 254 may extend circumferentially and axially in relation to axis 100.

The guide 230 of the distal placement portion 220 can be configured in many ways to guide a needle toward recess 231 when the insertion apparatus holds the implantable device with the engagement structure 250. The guide 230 can include the first side 222 and the second side 224. The guide 230 can include a plurality of recessed surfaces that allow a short needle to be used to place the therapeutic fluid including therapeutic agent 110 in the implantable device. The guide 230 can include a first proximal guide surface 232 and first intermediate guide surface 233, and a first distal guide surface 236 on the first side 222. The guide 230 can include a second proximal guide surface 234 and second intermediate guide surface 235, and a second distal guide surface 238 on the second side 224. The guide surfaces are arranged to provide a visual reference to a user advancing a needle and also provide a surface to support the needle connector and maintain alignment of the needle when placed.

The first extension 212 and the second extension 214 can be coupled to the distal placement portion 220 in many ways. The extensions can be coupled to the distal portion so that pressing the extensions together separates the first engagement structure 251 of the first side 222 from the second engagement structure 253 of the second side 224 as shown with arrows 228, for example (see FIGS. 3A and 3B). The extension 212 and the extension 214 can include springs such that the first engagement structure 251 is urged toward the second engagement structure 253 when the user gently grasps the extensions without urging the extensions inward. The first extension 212 on the first side 222 can extend transverse to axis 200A and affix to second side 224, and the second extension 214 can extend transverse to axis 200A and affix to first side 222, for example. Alternatively, the first extension 212 and the second extension 214 can be coupled to the distal placement portion 220 such that urging the extensions toward each other urges the first engagement structure 251 toward the second engagement structure 253 so as to hold the implantable device 100, and such that releasing the extensions separates the first engagement structure 251 from the second engagement structure 253 with resilient spring force so as to release the implantable device 100. The first extension 212 can extend and affix to first side 222 of the distal placement portion 220, and the second extension 214 can extend and affix to second side 224, for example.

The first extension 212 and the second extension 214 can be affixed to the distal placement portion 220 in many ways. Fasteners 226 can be used to couple the extensions to the distal placement portion, for example.

Figure 3B:
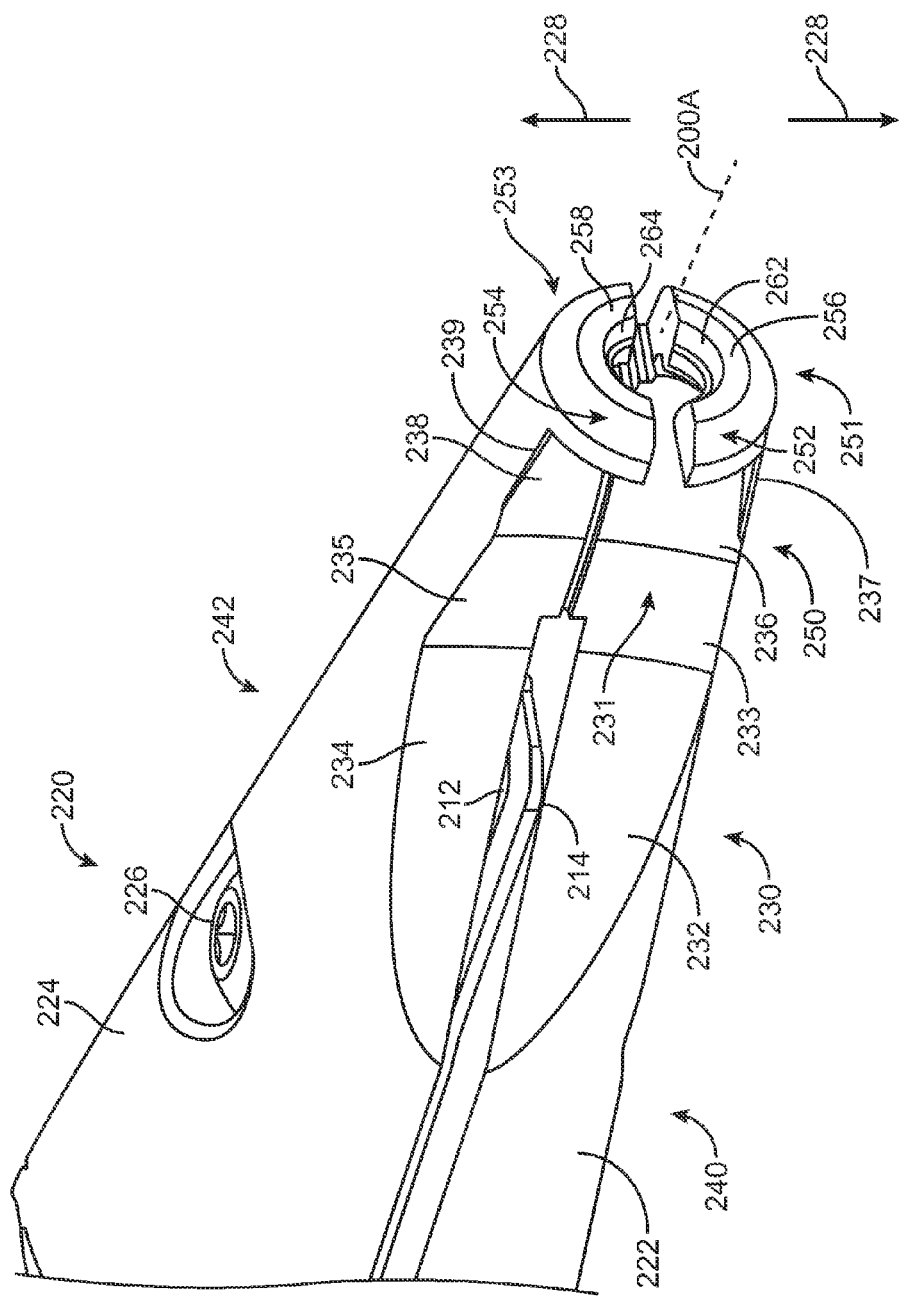
FIGS. 3B and 3C show front and back views, respectively, of a distal placement portion of the insertion apparatus of FIG. 3A.
Figure 3C:
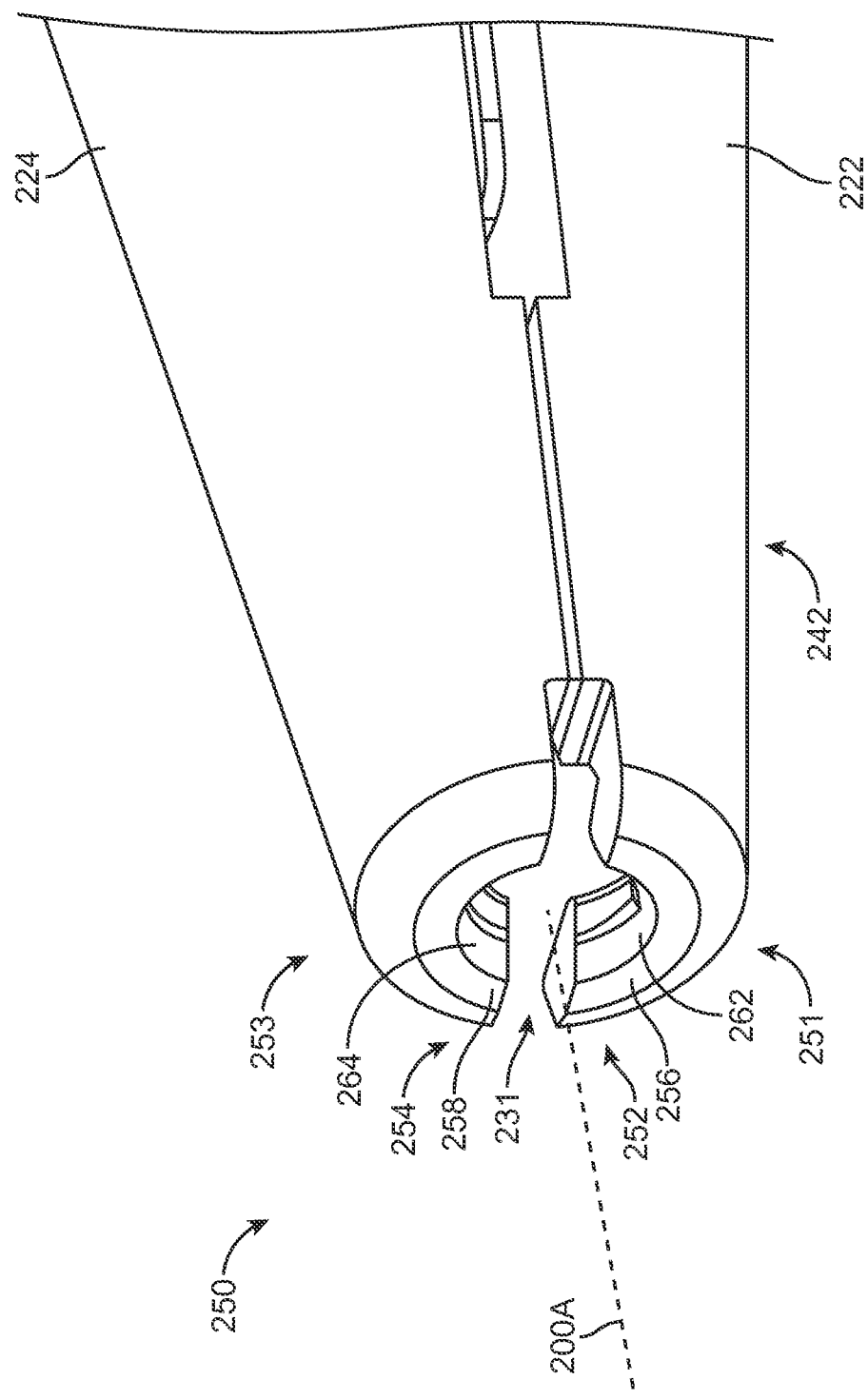

FIGS. 3B and 3C show front and back views, respectively, of a distal placement portion of the insertion apparatus of FIG. 3A. The first engagement structure 251 includes a protrusion 262, and the second engagement structure 253 includes a protrusion 264. The protrusion 262 and the protrusion 264 are sized to fit in one or more recesses, such as the narrow region, of the implantable device to retain the implantable device. The protrusion 262 includes a distal surface 256 to engage the shoulder of the implantable device, and the opposing protrusion 264 includes a distal surface 258 to engage the implantable device on an opposite side. The projection 252 can include a flange 237, and the projection 254 can include a support flange 239.

The first extension 212 can be affixed to the second side 224 of the distal placement portion 220, and the second extension 214 can be affixed to the first side 222 of the distal placement portion 220.

Figure 3D:
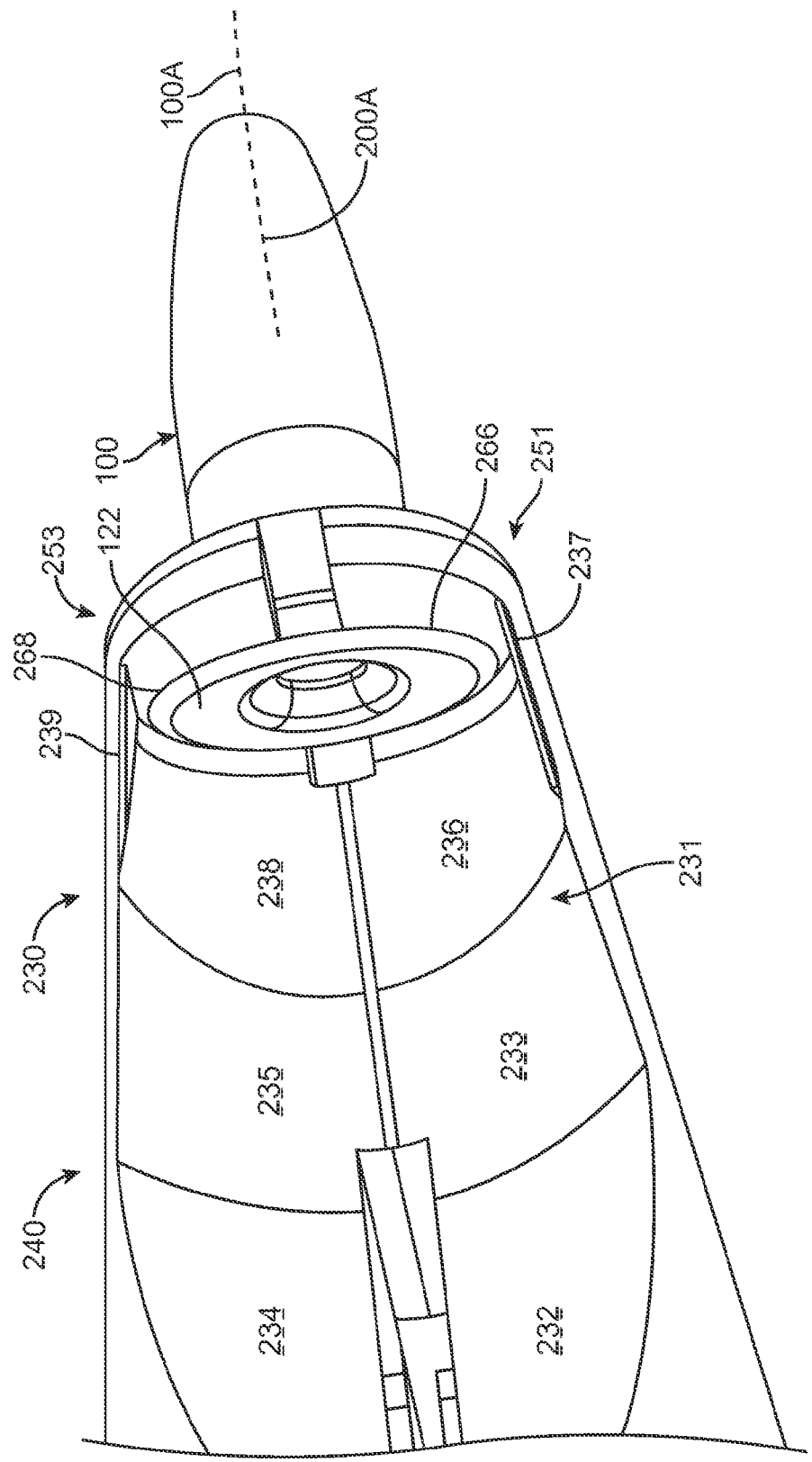
FIGS. 3D and 3E show front and back views, respectively, of the distal placement portion of the insertion apparatus engaging the implantable device.
Figure 3E:
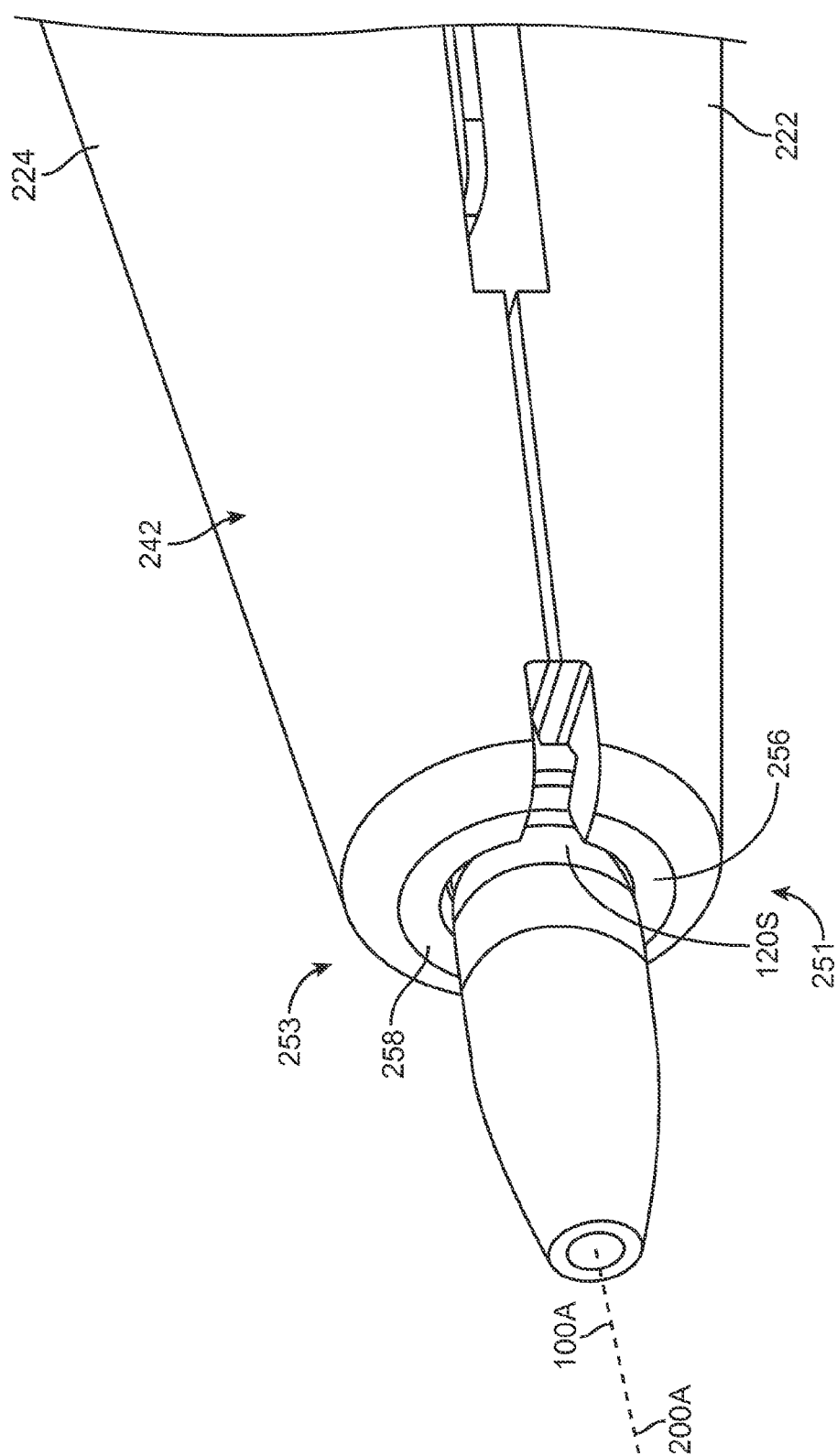

FIG. 3D and FIG. 3E show the implantable device 100 and the distal placement portion 220 of the insertion apparatus 200 (FIG. 3A), the retention structure 120 (FIG. 2E) of the implantable device 100 can be aligned with the engagement structure 250 (FIG. 3A). The retention structure 120 includes a narrow portion 120N (FIG. 2E) dimensioned to receive the protrusion 262 and the protrusion 264 (FIG. 3C) to hold the implantable device. The protrusion 262 and the protrusion 264 (FIG. 3C) can be shaped in many ways to engage the narrow portion 120N (FIG. 2E), and can include lentoid, oval, elliptical or circular structures. In many embodiments, the protrusion 262 and the protrusion 264 (FIG. 3C) include a structure similar to the shape profile or outer contour of the narrow portion 120N (FIG. 2E), and can include circular structures when the narrow portion 120N (FIG. 2E) includes a circular cross section, for example. In many embodiments, the narrow portion 120N (FIG. 2E) includes one or more an oval, elliptical or lentoid geometry, and the protrusion 262 and the protrusion 264 (FIG. 3C) include a corresponding geometry, for example.

The first protrusion 262 on first engagement structure 251 (FIG. 3C) can include a proximal surface 266 to engage a distal surface of the extension 122 of the retention structure 120 (FIG. 3D), and the second protrusion 264 on the second engagement structure 253 can include a proximal surface 268 to engage the distal surface of the extension 122 of the retention structure 120, for example (FIG. 3C and FIG. 3D). The first engagement structure 251 can be urged toward the second engagement structure 253 to slide the first protrusion 262 and the second protrusion 264 (FIG. 3C) into the indentation 120N of the retention structure 120 (FIG. 2E).

FIGS. 3D and 3E show front and back views, respectively, of the distal placement portion 220 of the insertion apparatus 200 (FIG. 3A) engaging the implantable device 100. The first engagement structure 251 and the second engagement structure 253 extend substantially around the retention structure 120 (FIG. 2E) to hold the implantable device 100. FIG. 3D shows the extension 122 of the retention structure, as the rest of the retention structure is obscured from view by the first and second engagement structures, 251 and 253, respectively. FIG. 3E shows the shoulder 120S of the retention structure, as the rest of the retention structure is obscured from view by the first and second engagement structures, 251 and 253, respectively. The implantable device 100 is held such that the axis 100A of the implantable device is aligned substantially with the axis 200A of the insertion apparatus. The implantable device 100 can be held with the axis 100A substantially concentric with the axis 200A of the insertion apparatus 200, for example. FIG. 3D also shows elements of the distal placement portion 220 shown in FIG. 3B and described herein above, such as the recess 231; the guide 230 that may have first and second proximal guide surfaces (232 and 234, respectively), first and second intermediate guide surfaces (233 and 235, respectively), and first and second distal guide surfaces (236 and 238, respectively); and the support flanges 239 and 237. FIG. 3E also shows the distal surfaces 256 and 258 of the engagement structures 251 and 253, respectively.

Figure 3F:
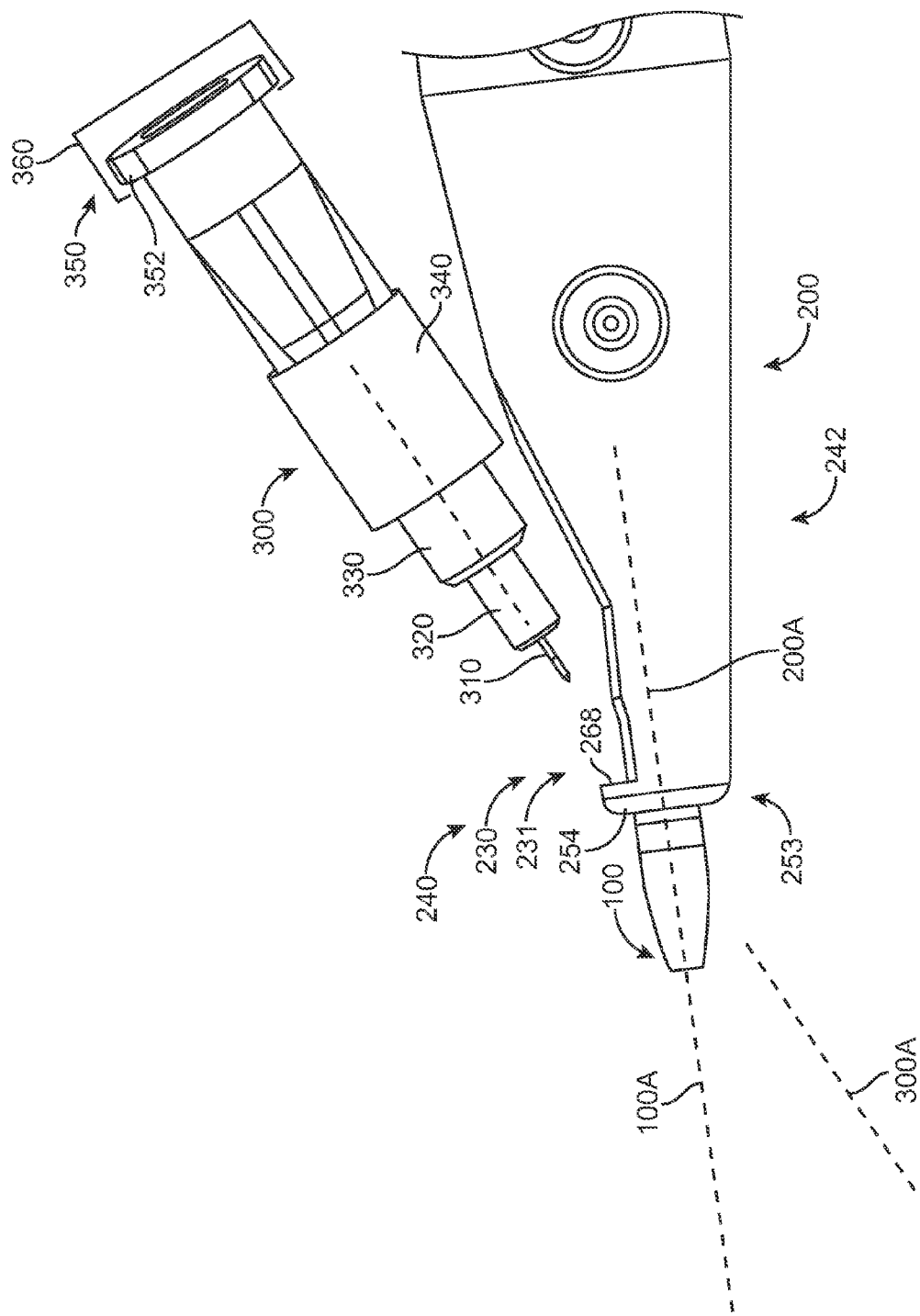
FIG. 3F shows an injector having a needle advanced toward the implantable device held with the insertion apparatus, in accordance with embodiments.

FIG. 3F shows an injector 300 having a needle 310 advanced toward the implantable device 100 held by the insertion apparatus 200. The injector 300 can include needle 310 and a syringe 360, for example. The needle 310 can be coupled to the syringe 360 with a connector 350. The connector 350 can include extensions 352 to couple the needle to the syringe 360. The syringe 360 and the needle 310 may extend substantially along an axis 300A. The needle 310 can include a housing 340. The housing 340 can include a plurality of structures to couple to or engage with the guide 230, such that the needle 310 can be advanced along axis 300A toward the proximal end of the implantable device 100. The plurality of structures of the housing 340 can include a first structure 320, a second structure 330, for example. The guide 230 and housing 340 can be configured to align the axis 300A of the needle 310 oblique to the axis 100A of the implantable device and the axis 200A of the insertion apparatus when the needle 310 advances toward the penetrable barrier of the implantable device 100. FIG. 3F also shows the recess 231, the second projection 254, and the proximal surface 268 of the engagement structure.

Figure 3G:
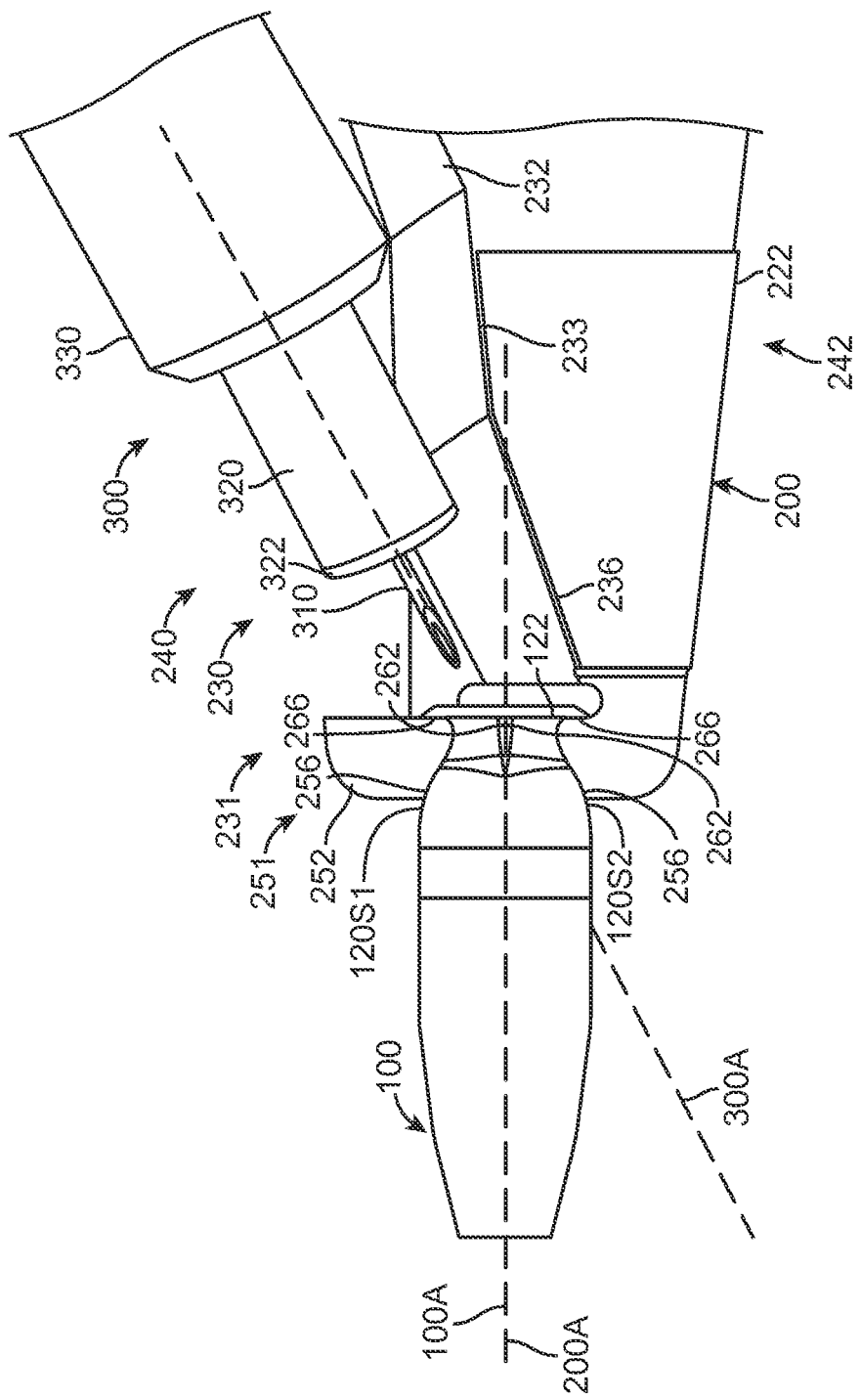
FIG. 3G shows a side view of the implantable device held with one of the engagement structures and the needle aligned obliquely with the axis of the implantable device, in accordance with embodiments.

FIG. 3G shows a side view of the implantable device 100 held with one of the engagement structures 251 and the needle 310 aligned obliquely with the axis 100A of the implantable device. The protrusion 262 extends substantially into the narrow portion 120N of retention structure 120 (FIG. 2E). The distal surface 256 of the protrusion 262 engages the shoulder 120S. The proximal surface 266 of the protrusion 262 of engages the distal surface of the extension 122 of the retention structure 120. The shoulder 120S can include a first shoulder 120S1 and a second shoulder 120S2 on first and second sides, respectively, of the retention structure 120 as described herein, for example.

In many embodiments, the second engagement structure 253 includes structure similar to the first engagement structure 251 as described herein.

Figure 3H:
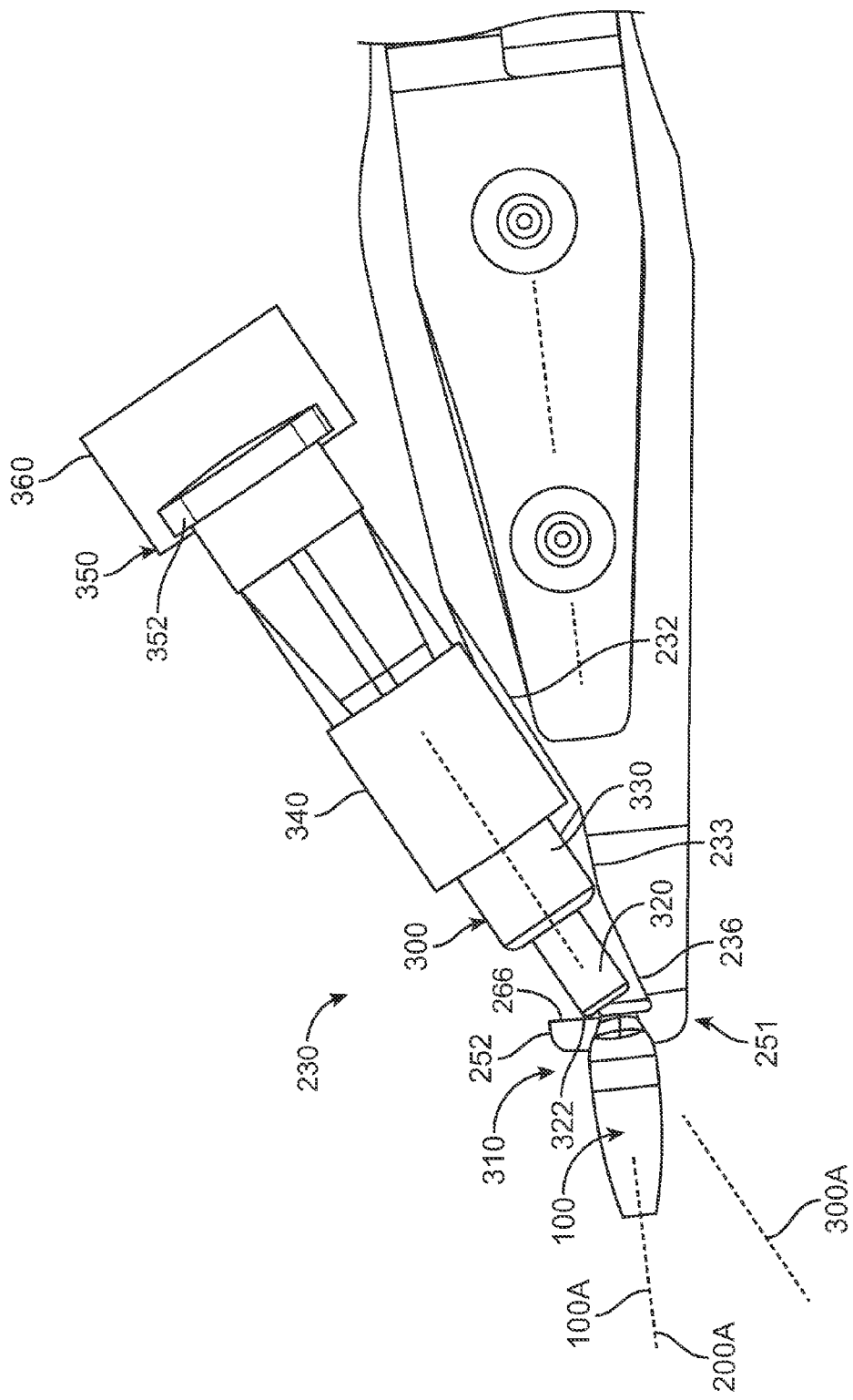
FIG. 3H shows the needle inserted obliquely into the implantable device to inject the therapeutic agent, in accordance with embodiments.

FIG. 3H shows the needle inserted obliquely into the implantable device 100, for example to inject the therapeutic agent. The implantable device can include penetrable barrier 184 (FIG. 2E) having a first outer surface facing the syringe 360 and a second inner surface and a thickness extending between the first surface and the second surface. The needle 310 can pass through the penetrable barrier 184 at an angle away from perpendicular to the surfaces such that the needle 310 extends within the penetrable barrier 184 a distance greater than the thickness 184D (shown in FIG. 2G). The housing 340 can be aligned substantially with the guide 230 so as to support the housing 340 with the guide 230 when the needle 310 extends through the penetrable barrier 184. For example the surface 232 can be aligned substantially with the outer surface of the casing 340. A distal portion of the surface 233 can be aligned substantially with a distal portion of the structure 330. A distal portion 322 of the structure 320 can engage the proximal surface 266 so as to limit penetration of the needle 310 into the implantable device, for example.

Figure 4A:
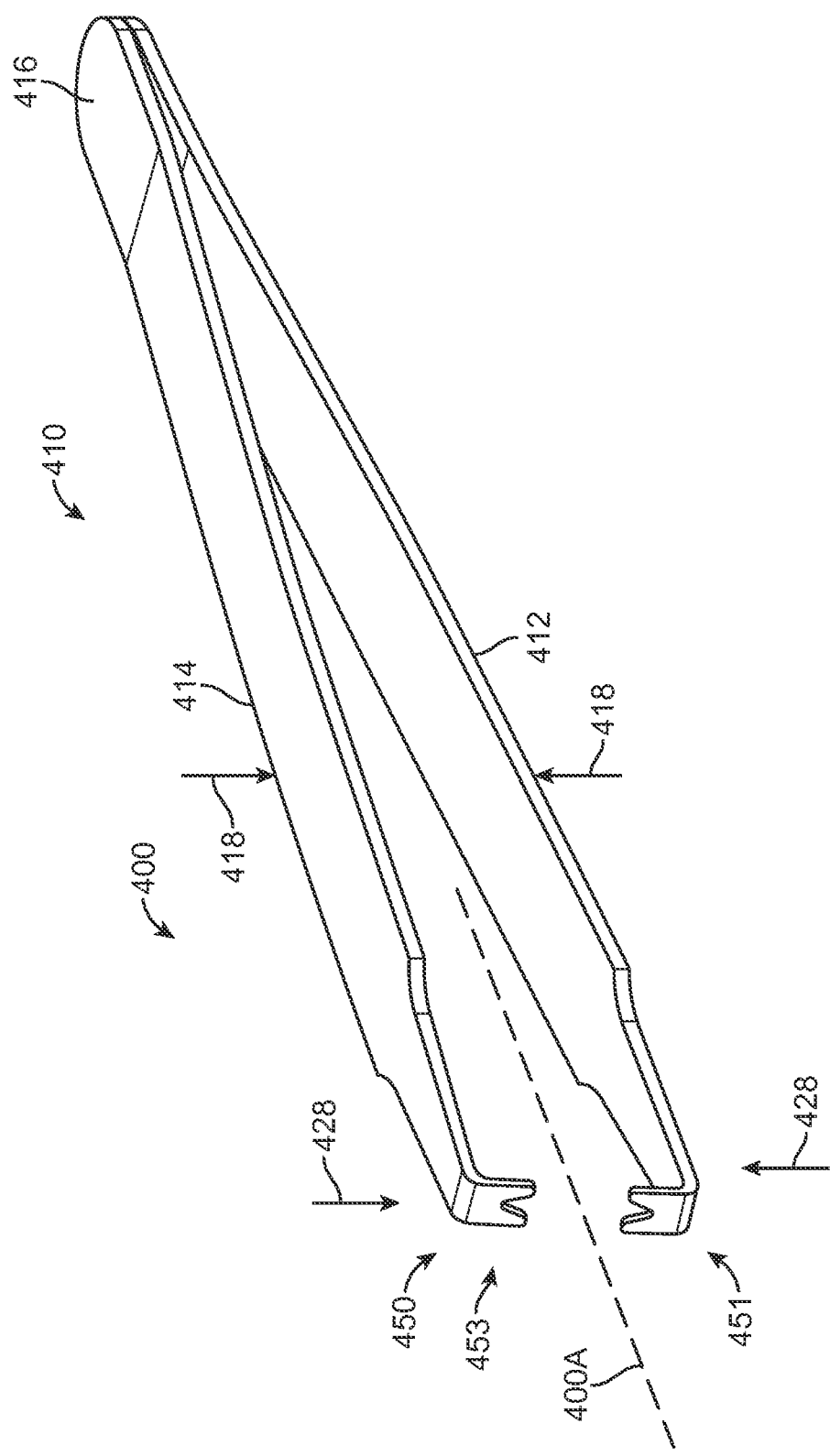
FIG. 4A shows a removal tool, in accordance with embodiments.

FIG. 4A shows a removal tool 400. The removal tool 400 can include a handle 410 and an engagement structure 450. The engagement structure 450 can include a first engagement structure 451 and a second engagement structure 453. The first engagement structure 451 can be located on a first side of axis 400A, and the second engagement structure 453 can be located on a second side of axis 400A opposite the first engagement structure 451. The handle 410 can be configured in many ways and can include a first extension 412 and a second extension 414. The first extension 412 and the second extension 414 may extend along opposite sides of an axis 400A. The extension 412 can be connected to the extension 414 at a proximal end 416. The extensions can be connected in many ways, for example with weld. The extension 412 and the extension 414 can include resilient material such that each extension includes a component of a spring. The first extension 412 can be urged toward the second extension 414 as shown with arrows 418, such that the first engagement structure 451 is urged toward the second engagement structure 453 as shown with arrows 428, for example. Alternatively, the engagement structures can be connected to the extensions in many alternative ways as described herein, for example.

FIG. 4B shows the removal tool of FIG. 4A aligned with an implantable device 100. The conjunctiva and a Tenon's of the eye can be removed so as to expose device 100, which can be aligned with the removal tool 400 as shown.

The first engagement structure 451 includes a first projection 452 and a second projection 456 which extend toward axis 400A, so as to define a channel 482 sized to receive the indentation 120N of the implantable device 100. The first projection 452 includes a tapered portion 462 extending to a leading edge 472. The second projection 456 includes a tapered portion 466 extending to a leading edge 476. The leading edges are configured to slide under the extension 122 of the retention structure 120.

The second engagement structure 453 includes a first projection 454 and a second projection 458 which extend toward axis 400A, so as to define a channel 484 sized to receive the indentation 120N of the implantable device 100. The first projection 454 includes a tapered portion 464 extending to a leading edge 474. The second projection 458 includes a tapered portion 468 extending to a leading edge 478. The leading edges are configured to slide under the extension 122 of the retention structure 120 opposite the leading edges of the engagement structure 451.

The axis 400A of the removal apparatus 400 can be aligned with the axis 100A of the implantable device 100 when the engagement structures are urged toward each other.

Figure 4C:
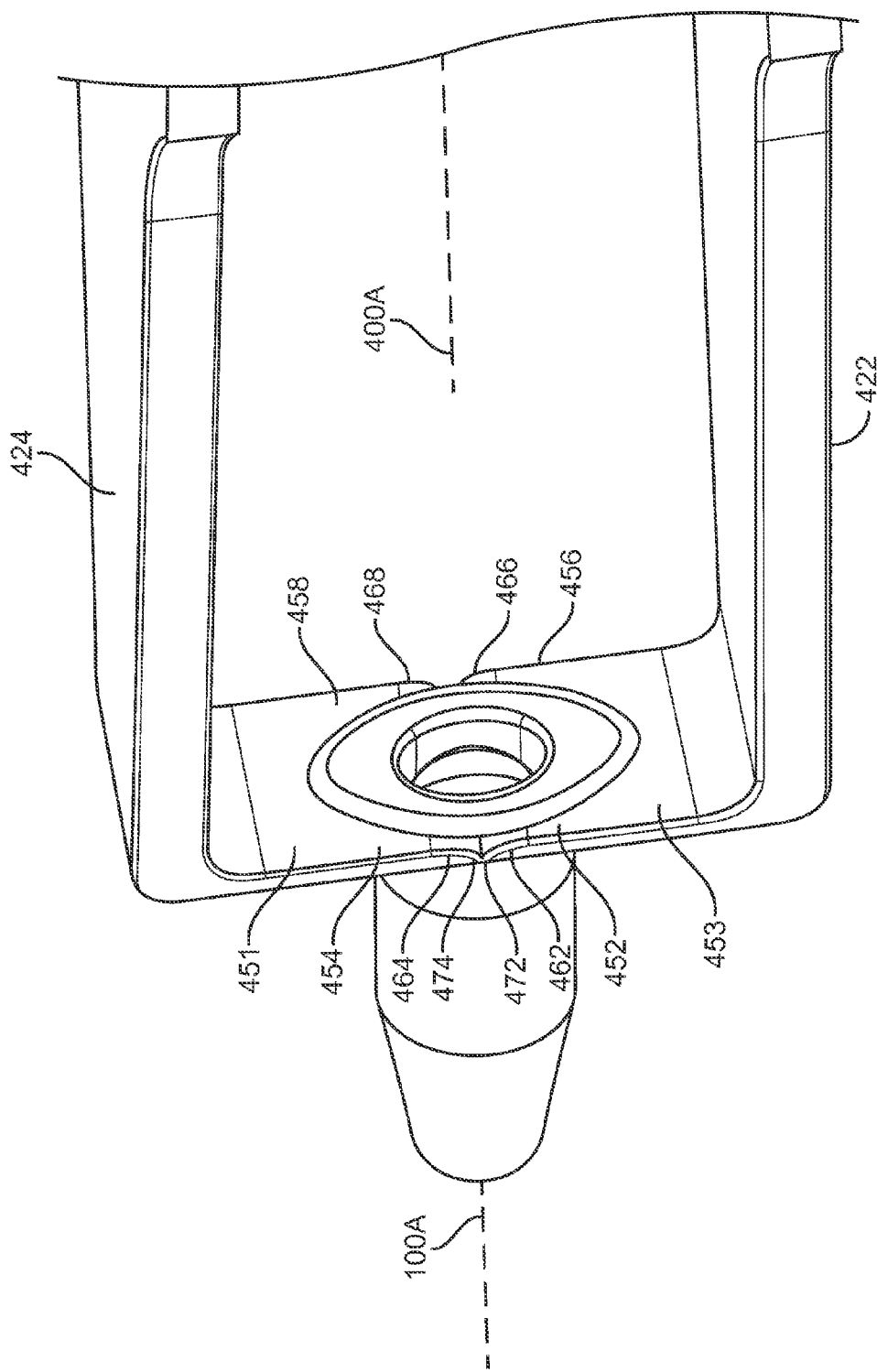
FIGS. 4C and 4D show top and bottom views, respectively, of the removal tool of FIGS. 4A and 4B holding the implantable device, in accordance with embodiments.
Figure 4D:
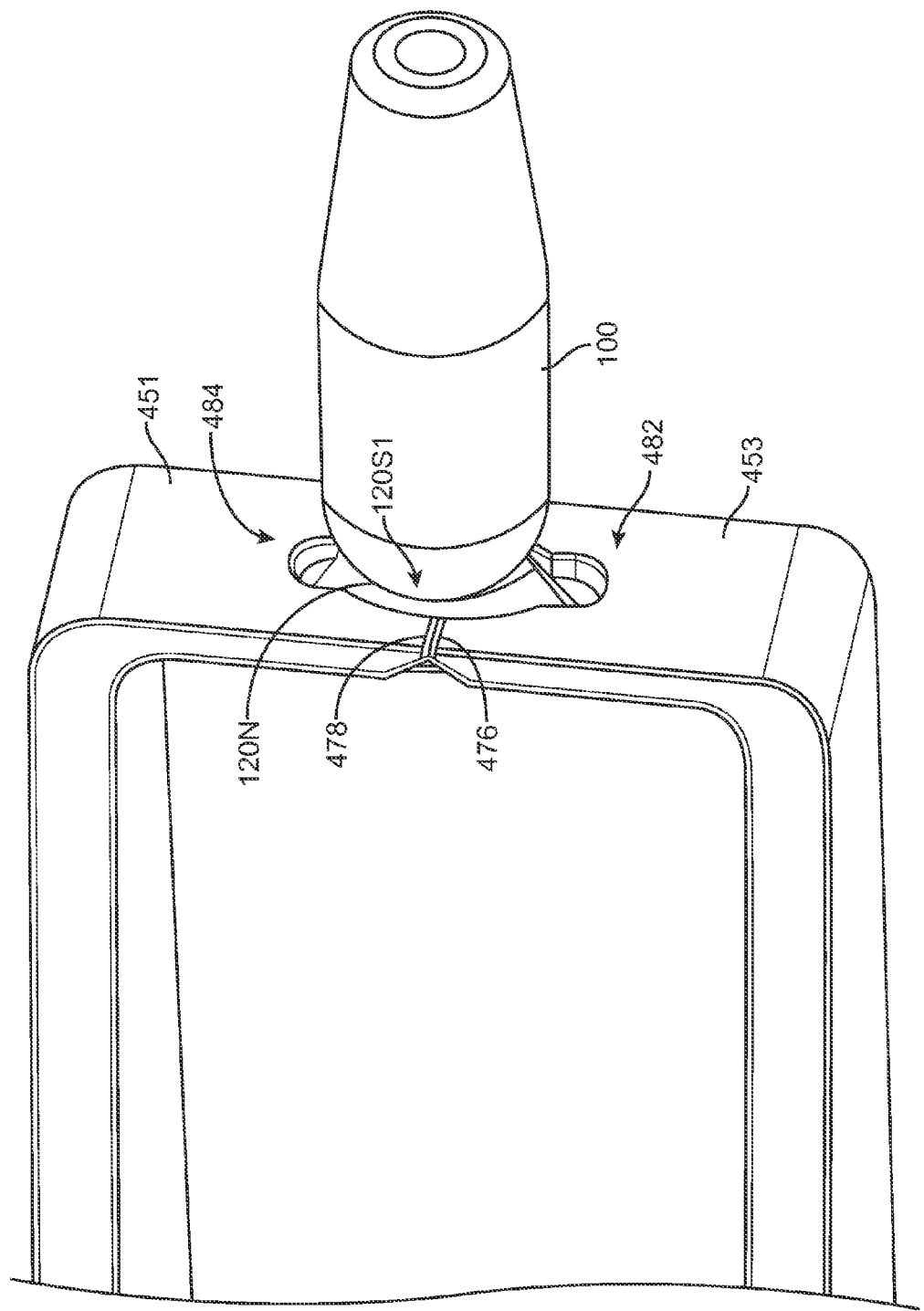

FIGS. 4C and 4D show top and bottom views, respectively, of the removal tool 400 of FIGS. 4A and 4B holding the implantable device 100. The leading edge 472, adjacent to tapered portion 462, engages the leading edge 474, adjacent to tapered portion 464, so as to define a first stop, and the leading edge 476, adjacent to tapered portion 466, engages the leading edge 478, adjacent to tapered portion 468, so as to define a second stop. The channel 482 and the channel 484 are sized to provide a gap extending around the narrow portion 120N when leading edges of engagement structure 451 engage the leading edges of the engagement structure 453. The removal tool engages extension 122 of the retention structure 120 (FIG. 2E) with the proximal surfaces of projection 452, projection 454, projection 456 and projection 458, and the gap provides clearance to inhibit pinching of the narrow portion 120N of the retention structure. FIG. 4D also shows a shoulder 120S1 of the retention structure 120 in relation to the engagement structures 451 and 453.

The retention structure 120 and the narrow portion 120N (FIG. 2A-G) of the retention structure can be configured in many ways as described herein. In many embodiments, the long distance of the retention structure 120N is aligned such that the projections slide under the extension 122 in alignment with the long distance of the narrow portion 120N. Alternatively, the short distance of the retention structure 120N may be aligned such that the projections slide under the extension 122 in alignment with the short distance of the narrow portion 120N. A person of ordinary skill in the art will recognize many variations based on the teachings and embodiments described herein, and the narrow portion 120N can include a substantially circular cross-sectional area, for example.

The removal tool 400 can be fabricated in many ways. For example, removal tool 400 can include a unitary structure. Alternatively, the extension and engagement structure of each side can include a unitary structure fabricated from a single piece of material, and the two unitary structures can be joined together at the proximal end 416 for example with a weld as described herein, for example.

Figure 4E:
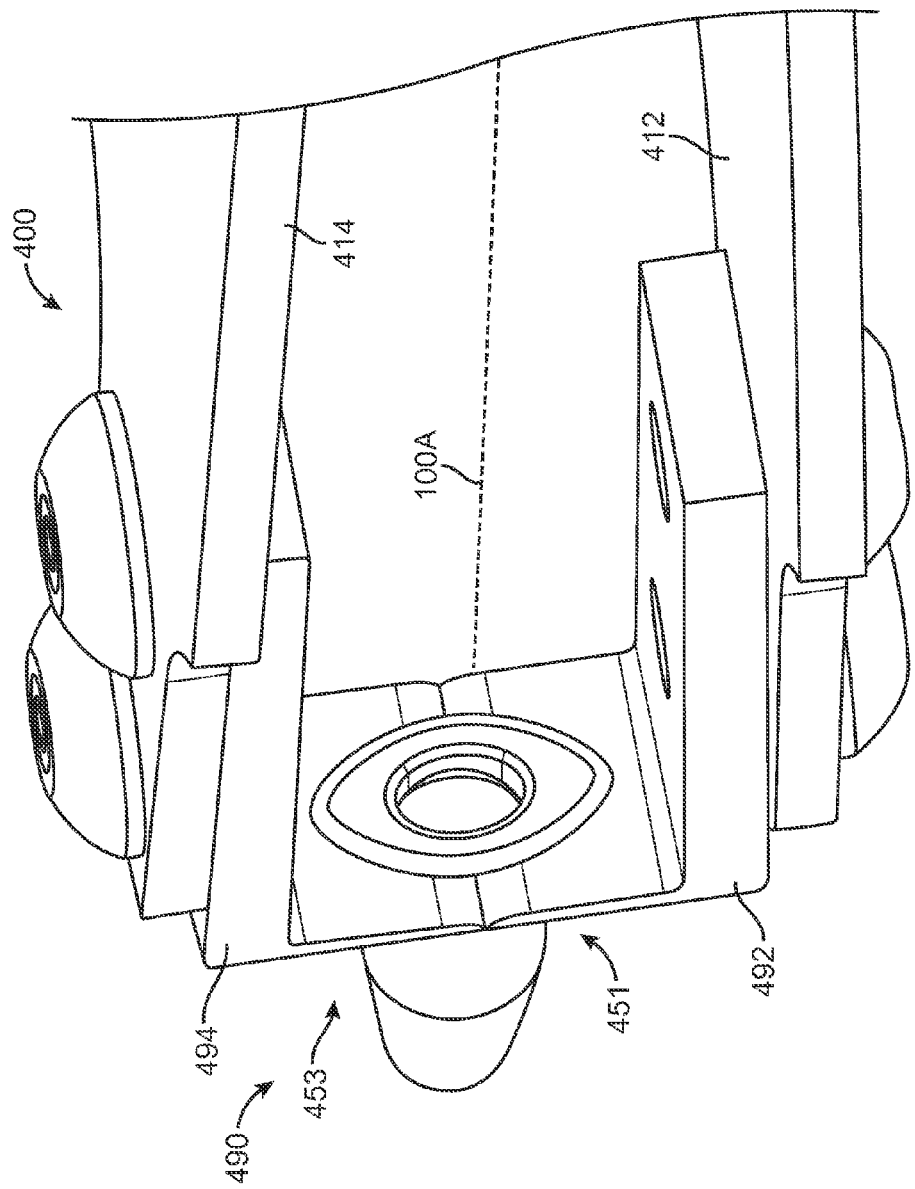
FIG. 4E shows the removal tool having opposing components, in accordance with embodiments.

FIG. 4E shows the removal tool 400 having opposing components 490 holding a device with an alignment axis, 100A. The opposing components 490 can include a first component 492 having first engagement structure 451, and a second component 494 having second engagement structure 453. The first component 492 can be affixed to first extension 412 and the second component 494 can be affixed to the second extension 414, for example.

FIGS. 5A to 5D show a method 500 of placing therapeutic device 100 in an eye 10.

FIG. 5A shows a step 510. At step 510, an injector apparatus 300 having a needle is inserted into the implantable device 100 containing air 70. The device 100 is held by an insertion apparatus 200, and the injector apparatus 300 fits into the guide 230 of the insertion apparatus 200. The insertion of the needle into the device 100 can be viewed through a binocular operating microscope 505. The needle can be inserted with the guide 230 into the recess as described herein when viewed through microscope 505.

FIG. 5B shows a therapeutic fluid 119 having therapeutic agent 110 placed in the implantable device 100 at a step 520. The therapeutic fluid can include a flowable material, for example a solution. The wall of the reservoir chamber of the therapeutic device 100 can include a substantially transparent material so that the flow of the fluid 119 toward the porous structure 150 on the distal end can be visualized.

FIG. 5C shows the therapeutic fluid injected such that some therapeutic fluid flows through a porous structure on the distal end of the implantable device of FIG. 5A at a step 530. The therapeutic fluid 119, containing the therapeutic agent 110, can be injected through the porous structure 150 so as to accumulate on the distal end of device 100. The accumulation of fluid 119 on the distal end can indicate to the physician that the reservoir chamber of device 100 has been filled. The physician can inspect the device 100 for air bubbles, for example, so as to ensure the device has been filled properly.

FIG. 5D shows the implantable device 100 being placed in the eye 10 with insertion apparatus 200 at a step 540. The device 100 filled with therapeutic agent 110 can be implanted at the pars plana region 20 as described herein. The conjunctiva can be removed from the sclera, and the device 100 placed in the eye. The conjunctiva can be placed over device 100 and the conjunctiva sutured in place. Device 100 is configured such that a layer of Tenon's capsule can grow over the extension 122 of device 100 to retain device 100.

Figure 6A:
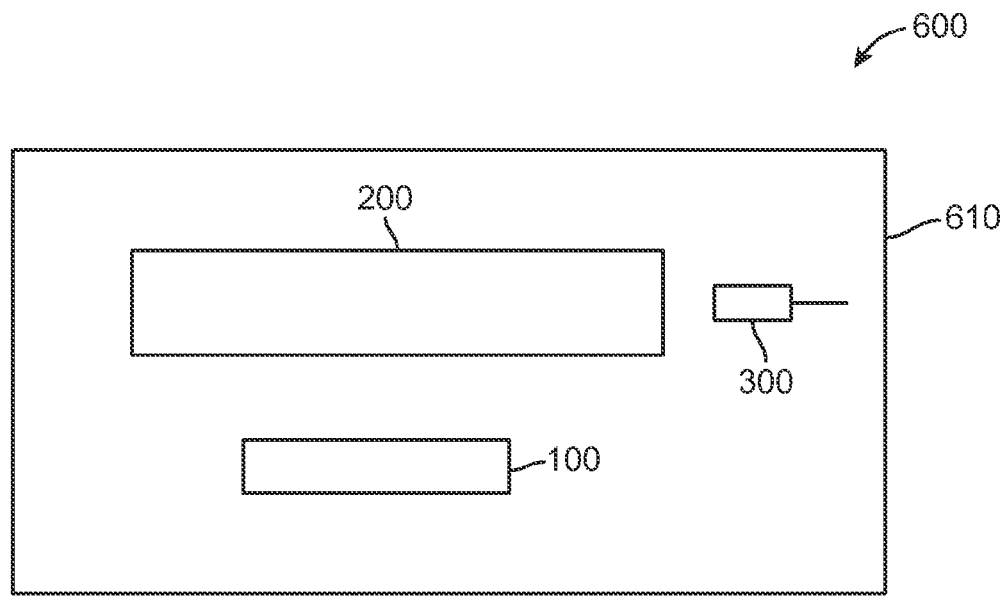
FIG. 6A shows a kit having an insertion apparatus, in accordance with embodiments.

FIG. 6A shows a kit 600 having an insertion apparatus 200 and sterile packaging 610. The kit 600 can include the insertion apparatus 200 and the device 100 placed in the packaging. The retention structure of the device 100 can be mounted in the engagement structure of the apparatus 200 as described herein when provided in the kit. Alternatively, the device 100 can be within sterile packaging 610 separated from apparatus 200, and the device 100 engaged with apparatus 200 after the sterile kit has been opened, for example. The kit 600 can include the injector apparatus 300.

Figure 6B:
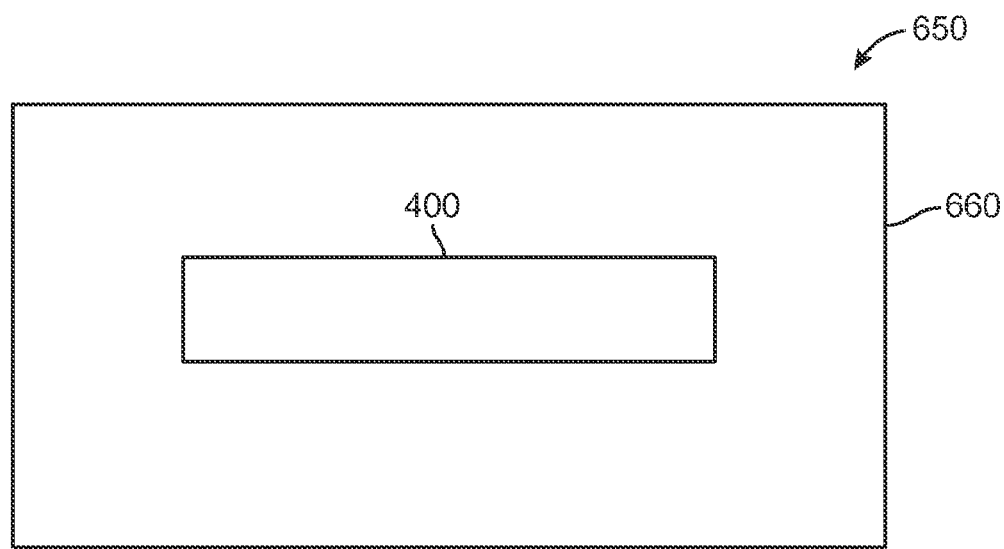
FIG. 6B shows a kit having a removal tool, in accordance with embodiments.

FIG. 6B shows a kit 650 including a removal tool 400. The kit 650 can include sterile packaging 660 to protect removal apparatus 400.

While the exemplary embodiments have been described in some detail, by way of example and for clarity of understanding, those of skill in the art will recognize that a variety of modifications, adaptations, and changes may be employed. Hence, the scope of the present disclosure shall be limited solely by the appended claims.

TABLE 1A

Therapeutic Agent List

| Generic Name | Brands (Companies) | Category | Indication | Molecular Weight |
|---|---|---|---|---|
| 2-Methoxyestradiol analogs | (Paloma Pharmaceuticals) | Angiogenesis inhibitors | AMD | |
| 3-aminothalidomide | | | | |
| 13-cis retinoic acid | Accutane TM (Roche Pharmaceuticals) | | | |
| A0003 | (Aqumen BioPharmaceuticals) | A0003 | AMD | |
| A5b1 integrin inhibitor | (Jerini Ophthalmic); (Ophthotech) | Inhibitors of a5b1 integrin | AMD | |
| Abarelix | Plenaxis ™ (Praecis Pharmaceuticals) | Anti-Testosterone Agents; Antineoplastic Agents | For palliative treatment of advanced prostate cancer. | 37731 |
| Abatacept | Orencia ™ (Bristol-Myers Squibb) | Antirheumatic Agents | For the second line reduction of the signs and symptoms of moderate-to-severe active rheumatoid arthritis, inducing major clinical response, slowing the progression of structural damage, and improving physical function in adult patients who have | 37697 |
| Abciximab | ReoPro ™; ReoPro ™ (Centocor) | Anticoagulants; Antiplatelet Agents | For treatment of myocardial infarction, adjunct to percutaneous coronary intervention, unstable angina | 42632 |
| ABT-578 | (Abbott Laboratories) | Limus Immunophilin Binding Compounds | | |
| Acetonide | | | | |
| Adalimumab | Humira ™ (Abbott Laboratories) | Antirheumatic Agents; Immunomodulatory Agents | Uveitis, AMD | 25645 |
| Aldesleukin | Proleukin ™; Proleukin ™ (Chiron Corp) | Antineoplastic Agents | For treatment of adults with metastatic renal cell carcinoma | 61118 |
| Alefacept | Amevive ™ | Immunomodulatory Agents; Immunosuppressive Agents | For treatment of moderate to severe chronic plaque psoriasis | 42632 |
| Alemtuzumab | Campath ™; Campath ™ (ILEX Pharmaceuticals LP); MabCampath ™ | Antineoplastic Agents | For treatment of B-cell chronic lymphocytic leukemia | 6614 |
| Alpha-1-proteinase inhibitor | Aralast ™ (Baxter); Prolastin ™ (Talecris Biotherapeutics C formerly Bayer) | Enzyme Replacement Agents | For treatment of panacinar emphysema | 28518 |
| Alteplase | Activase ™ (Genentech Inc) | Thrombolytic Agents | For management of acute myocardial infarction, acute ischemic stroke and for lysis of acute pulmonary emboli | 54732 |
| AMG-1470 | | | | |
| Anakinra | Kineret ™ (Amgen Inc) | Anti-Inflammatory Agents, Non-Steroidal; Antirheumatic Agents; Immunomodulatory Agents | For the treatment of adult rheumatoid arthritis. | 65403 |
| Anecortave acetate | | | | |
| Angiostatin | | | | |
| Anistreplase | Eminase ™ (Wulfing Pharma GmbH) | Thrombolytic Agents | For lysis of acute pulmonary emboli, intracoronary emboli and management of myocardial infarction | 54732 |
| Anti-angiogenesis peptides | (Eyecopharm) | Anti-angiogenesis peptides | AMD | |
| Anti-angiogenesis antibodies, TRC093, TRC105 | (TRACON Pharma) | Anti-angiogenesis antibodies | AMD | |

TABLE 1A-continued

Therapeutic Agent List

| Generic Name | Brands (Companies) | Category | Indication | Molecular Weight |
|---|---|---|---|---|
| Anti-angiogeric bifunctional protein | Icon-1 ™ (Iconic Therapeutics) | Anti-angiogeric bifunctional protein, Icon-1 | AMD | |
| Anti-endothelial growth factor | | | | |
| Antihemophilic Factor | Advate ™; Alphanate ™; Bioclate ™; Helixate ™; Helixate FS ™; Hemofil M ™; Humate-P ™; Hyate:C ™; Koate-HP ™; Kogenate ™; Kogenate FS ™; Monarc-M ™; Monoclate-P ™; ReFacto ™; Xyntha ™ | Coagulants; Thrombotic Agents | For the treatment of hemophilia A, von Willebrand disease and Factor XIII deficiency | 70037 |
| Antithymocyte globulin | Genzyme); Thymoglobulin ™ (SangStat Medical | Immunomodulatory Agents | For prevention of renal transplant rejection | 37173 |
| Anti-hypertensive MC1101 | (MacuCLEAR) | Anti-hypertensive MC1101 | AMD | |
| Anti-platelet devired growth factor | | | | |
| Anti-VEGF | (Neurotech); Avastin ™ (NeoVista) | Anti-VEGF | AMD | |
| AP23841 | (Ariad) | Limus Immunophilin Binding Compounds | | |
| ARC1905 | Ophthotech | Complement Cascade Inhibitor (Factor C5) | | |
| Aprotinin | Trasylol ™ | Antifibrinolytic Agents | For prophylactic use to reduce perioperative blood loss and the need for blood transfusion in patients undergoing cardiopulmonary bypass in the course of coronary artery bypass graft surgery who are at an increased risk for blood loss and blood transfusion | 90569 |
| Arcitumomab | CEA-Scan ™ | Diagnostic Agents; Imaging Agents | For imaging colorectal tumors | 57561 |
| Asparaginase | Elspar ™ (Merck & Co. Inc) | Antineoplastic Agents | For treatment of acute lymphocytic leukemia and non-Hodgkins lymphoma | 132.118 |
| Axitinib | | Tyrosine Kinase Inhibitors | | 386 |
| Basiliximab | Simulect ™ (Novartis Pharmaceuticals) | Immunomodulatory Agents; Immunosuppressive Agents | For prophylactic treatment of kidney transplant rejection | 61118 |
| Becaplermin | Regranex ™; Regranex ™ (OMJ Pharmaceuticals) | Anti-Ulcer Agents; Topical | For topical treatment of skin ulcers (from diabetes) | 123969 |
| Bevacizumab | Avastin ™; Avastin ™ (Genentech Inc) | Antiangiogenesis Agents; Antineoplastic Agents | For treatment of metastatic colorectal cancer | 27043 |
| Bivalirudin | Angiomax ™; Angiomax ™ (Medicines Co or MDCO); Angiox ™ | Anticoagulants; Antithrombotic Agents | For treatment of heparin-induced thrombocytopenia | 70037 |
| Bortezomib | | Proteosome Inhibitors | | |
| Bosutinib | | Tyrosine Kinase Inhibitors | | 530 |
| Botulinum Toxin Type A | BOTOX ™ (Allegran Inc); BOTOX Cosmetic ™ (Allegran Inc); Botox ™; Dysport ™ | Anti-Wrinkle Agents; Antidystonic Agents; Neuromuscular Blocking Agents | For the treatment of cervical dystonia in adults to decrease the severity of abnormal head position and neck pain associated with cervical dystonia. Also | 23315 |

TABLE 1A-continued

Therapeutic Agent List

| Generic Name | Brands (Companies) | Category | Indication | Molecular Weight |
|---|---|---|---|---|
| Botulinum Toxin Type B | Myobloc ™ (Solstice Neurosciences); Neurobloc ™ (Solstice Neurosciences) | Antidystonic Agents | for the treatment of severe primary axillary hyperhidrosis that is inadequately managed with topical For the treatment of patients with cervical dystonia to reduce the severity of abnormal head position and neck pain associated with cervical dystonia. | 12902 |
| C5 inhibitor | (Jerini Ophthalmic); (Ophthotech) | Inhibitors of C5 | AMD | |
| Cal101 | Calistoga | PI3Kdelta Inhibitor | AMD, DME | |
| Canstatin | | | | |
| Capromab | ProstaScint ™ (Cytogen Corp) | Imaging Agents | For diagnosis of prostate cancer and detection of intra-pelvic metastases | 84331 |
| Captopril | | ACE Inhibitors | | |
| CCI-779 | (Wyeth) | Limus Immunophilin Binding Compounds | | |
| Cediranib | | Tyrosine Kinase Inhibitors | | 450 |
| Celecoxib | | Cyclooxygenase Inhibitors | | |
| Cetrorelix | Cetrotide ™ | Hormone Antagonists; Infertility Agents | For the inhibition of premature LH surges in women undergoing controlled ovarian stimulation | 78617 |
| Cetuximab | Erbitux ™; Erbitux ™ (ImClone Systems Inc) | Antineoplastic Agents | For treatment of metastatic colorectal cancer. | 42632 |
| Choriogonadotropin alfa | Novarel ™; Ovidrel ™; Pregnyl ™; Profasi ™ | Fertility Agents; Gonadotropins | For the treatment of female infertility | 78617 |
| Cilary neurotrophic factor | (Neurotech) | Ciliary neurotrophic factor | AMD | |
| Coagulation Factor IX | Benefix ™ (Genetics Institute) | Coagulants; Thrombotic Agents | For treatment of hemophilia (Christmas disease). | 267012 |
| Coagulation factor VIIa | NovoSeven ™ (Novo Nordisk) | Coagulants; Thrombotic Agents | For treatment of hemorrhagic complications in hemophilia A and B | 54732 |
| Colchicines | | | | |
| Collagenase | Cordase ™; Santyl ™ (Advance Biofactures Corp); Xiaflextm ™ | Anti-Ulcer Agents; Topical | For treatment of chronic dermal ulcers and severe skin burns | 138885 |
| Complement factor H recombinant | (Optherion); (Taligen Therapeutics) | Complement factor H recombinant | AMD, Geographic Atrophy | |
| Compstatin derivative peptide, POT-4 | (Potentia Pharmaceuticals) | Complement Factor C3 Inhibitors; Compstatin Derivative Peptides | AMD | |
| Corticotropin | ACTH ™; Acethropan ™; Acortan ™; Acthar ™; Exacthin ™; H.P. Acthar Gel ™; Isactid ™; Purified cortrophin gel ™; Reacthin ™; Solacthyl ™; Tubex | Diagnostic Agents | For use as a diagnostic agent in the screening of patients presumed to have adrenocortical insufficiency. | 33927 |
| Cosyntropin | Cortrosyn ™; Synacthen depot ™ | Diagnostic Agents | For use as a diagnostic agent in the screening of patients presumed to have adrenocortical insufficiency. | 33927 |
| Cyclophilins | | Limus Immunophilin Binding Compounds | | |
| Cyclosporine | Gengraf ™ (Abbott labs); Neoral ™ (Novartis); Restasis ™; Restasis ™ (Allergan Inc); Sandimmune ™ (Novartis); Sangcya ™ | Antifungal Agents; Antirheumatic Agents; Dermatologic Agents; Enzyme Inhibitors; Immunomodulatory Agents; | For treatment of transplant rejection, rheumatoid arthritis, severe psoriasis | 32953 |

TABLE 1A-continued

Therapeutic Agent List

| Generic Name | Brands (Companies) | Category | Indication | Molecular Weight |
|---|---|---|---|---|
| Daclizumab | Zenapax ™ (Hoffmann-La Roche Inc) | Immunosuppressive Agents Immunomodulatory Agents; Immunosuppressive Agents | For prevention of renal transplant rejection; Uveitis | 61118 |
| Darbepoetin alfa | Aranesp ™ (Amgen Inc.) | Antianemic Agents | For the treatment of anemia (from renal transplants or certain HIV treatment) | 55066 |
| Dasatinib | | Tyrosine Kinase Inhibitors | | 488 |
| Defibrotide | Dasovas ™; Noravid ™; Prociclide ™ | Antithrombotic Agents | Defibrotide is used to treat or prevent a failure of normal blood flow (occlusive venous disease, OVD) in the liver of patients who have had bone marrow transplants or received certain drugs such as oral estrogens, mercaptopurine, and many others. | 36512 |
| Denileukin diftitox | Ontak ™ | Antineoplastic Agents | For treatment of cutaneous T-cell lymphoma | 61118 |
| Desmopressin | Adiuretin ™; Concentraid ™; Stimate ™ | Antidiuretic Agents; Hemostatics; Renal Agents | For the management of primary nocturnal enuresis and indicated as antidiuretic replacement therapy in the management of central diabetes insipidus and for the management of the temporary polyuria and polydipsia following head trauma or surgery in the pitu | 46800 |
| Dexamethasone | Ozurdex ™ (Allergan) | Glucocorticoid | DME, inflammation, macular edema following branch retinal vein occlusion (BRVO) or central retinal vein occlusion (CRVO) | 392 |
| Diclofenac | | Cyclooxygenase Inhibitors | | |
| Dithiocarbamate | | NFκB Inhibitor | | |
| Dornase Alfa | Dilor ™; Dilor-400 ™; Lufyllin ™; Lufyllin-400 ™; Neothylline ™; Pulmozyme ™ (Genentech Inc) | Enzyme Replacement Agents | For the treatment of cystic fibrosis. | 7656 (double strand) |
| Drotrecogin alfa | Xigris ™; Xigris ™ (Eli Lilly & Co) | Antisepsis Agents | For treatment of severe sepsis | 267012 |
| Eculizumab | Soliris ™; Soliris ™ (Alexion Pharmaceuticals) | Complement Cascade Inhibitor (Factor C5) | AMD | 188333 |
| Efalizumab | Raptiva ™; Raptiva ™ (Genentech Inc) | Immunomodulatory Agents; Immunosuppressive Agents | For the treatment of adult patients with moderate to severe chronic plaque psoriasis, who are candidates for phototherapy or systemic therapy. | 128771 |
| Endostatin | | | | |
| Enfuvirtide | Fuzeon ™; Fuzeon ™ (Roche Pharmaceuticals) | Anti-HIV Agents; HIV Fusion Inhibitors | For treatment of HIV AIDS | 16768 |
| Epoetin alfa | Epogen ™ (Amgen Inc.); Epogin ™ (Chugai); Epomax ™ (Elanex); Eprex ™ (Janssen-Cilag. | Antianemic Agents | For treatment of anemia (from renal transplants or certain HIV treatment) | 55066 |

TABLE 1A-continued

Therapeutic Agent List

| Generic Name | Brands (Companies) | Category | Indication | Molecular Weight |
|---|---|---|---|---|
| | Ortho Biologics LLC); NeoRecormon ™ (Roche); Procrit ™ (Ortho Biotech); Recormon ™ (Roche) | | | |
| Eptifibatide | Integrilin ™; Integrilin ™ (Millennium Pharm) | Anticoagulants; Antiplatelet Agents; Platelet Aggregation Inhibitors | For treatment of myocardial infarction and acute coronary syndrome. | 7128 |
| Erlotinib | | Tyrosine Kinase Inhibitors | | 393 |
| Etanercept | Enbrel ™; Enbrel ™ (Immunex Corp) | Antirheumatic Agents; Immunomodulatory Agents | Uveitis, AMD | 25645 |
| Everolimus | Novartis | Limus Immunophilin Binding Compounds, mTOR | AMD | |
| Exenatide | Byetta ™; Byetta ™ (Amylin/Eli Lilly) | | Indicated as adjunctive therapy to improve glycemic control in patients with Type 2 diabetes mellitus who are taking metformin, a sulfonylurea, or a combination of both, but have not achieved adequate glycemic control. | 53060 |
| FCFD4514S | Genentech/Roche | Complement Cascade Inhibitor (Factor D) | AMD, Geographic Atrophy | |
| Felypressin | Felypresina ™ [INN-Spanish]; Felypressina ™ [DCIT]; Felypressin ™ [USAN:BAN:INN]; Felypressine ™ [INN-French]; Felypressinum ™ [INN-Latin]; Octapressin ™ | Renal Agents; Vasoconstrictor Agents | For use as an alternative to adrenaline as a localizing agent, provided that local ischaemia is not essential. | 46800 |
| Fenretinide | Sirion/reVision Therapeutics | Binding Protein Antagonist for Oral Vitamin A | AMD, Geographic Atrophy | |
| Filgrastim | Neupogen ™ (Amgen Inc.) | Anti-Infective Agents; Antineutropenic Agents; Immunomodulatory Agents | Increases leukocyte production, for treatment in non-myeloid cancer, neutropenia and bone marrow transplant | 28518 |
| FK605-binding proteins, FKBPs | | Limus Immunophilin Binding Compounds | | |
| Fluocinolone Acetonide | Retisert ™ (Bausch & Lomb); Iluvien ™ (Alimera Sciences, Inc.) | Glucocorticoid | Retinal inflammation, diabetic macular edema | 453 |
| Follitropin beta | Follistim ™ (Organon); Gonal F ™; Gonal-F ™ | Fertility Agents | For treatment of female infertility | 78296 |
| Fumagillin | | | | |
| Galsulfase | Naglazyme ™; Naglazyme ™ (BioMarin Pharmaceuticals) | Enzyme Replacement Agents | For the treatment of adults and children with Mucopolysaccharidosis VI. | 47047 |
| Gefitinib | | Tyrosine Kinase Inhibitors | | 447 |
| Gemtuzumab ozogamicin | Mylotarg ™; Mylotarg ™ (Wyeth) | Antineoplastic Agents | For treatment of acute myeloid leukemia | 39826 |
| Glatiramer Acetate | Copaxone ™ | Adjuvants, Immunologic; Immunosuppressive Agents | For reduction of the frequency of relapses in patients with Relapsing-Remitting Multiple Sclerosis. | 29914 |
| Glucagon recombinant | GlucaGen ™ (Novo Nordisk); Glucagon ™ (Eli Lilly) | Antihypoglycemic Agents | For treatment of severe hypoglycemia, also used in gastrointestinal imaging | 54009 |

TABLE 1A-continued

Therapeutic Agent List

| Generic Name | Brands (Companies) | Category | Indication | Molecular Weight |
|---|---|---|---|---|
| Goserelin | Zoladex ™ | Antineoplastic Agents; Antineoplastic Agents, Hormonal | Breast cancer; Prostate carcinoma; Endometriosis | 78617 |
| Human Serum Albumin | Albutein ™ (Alpha Therapeutic Corp) | Serum substitutes | For treatment of severe blood loss, hypervolemia, hypoproteinemia | 39000 |
| Hyaluronidase | Vitragan ™; Vitrase ™; Vitrase ™ (Ista Pharma) | Anesthetic Adjuvants; Permeabilizing Agents | For increase of absorption and distribution of other injected drugs and for rehydration | 69367 |
| Ibritumomab | Zevalin ™ (IDEC Pharmaceuticals) | Antineoplastic Agents | For treatment of non-Hodgkin's lymphoma | 33078 |
| Idursulfase | Elaprase ™ (Shire Pharmaceuticals) | Enzyme Replacement Agents | For the treatment of Hunter syndrome in adults and children ages 5 and older. | 47047 |
| Imatinib | | Tyrosine Kinase Inhibitors | AMD, DME | 494 |
| Immune globulin | Civacir ™; Flebogamma ™ (Instituto Grifols SA); Gamunex ™ (Talecris Biotherapeutics) | Anti-Infectives; Immunomodulatory Agents | For treatment of immunodeficiencies, thrombocytopenic purpura, Kawasaki disease, gammablobulinemia, leukemia, bone transplant | 42632 |
| Infliximab | Remicade ™ (Centocor Inc) | Immunomodulatory Agents; Immunosuppressive Agents | Uveitis, AMD | 25645 |
| Insulin Glargine recombinant | Lantus ™ | Hypoglycemic Agents | For treatment of diabetes (type I and II) | 156308 |
| Insulin Lyspro recombinant | Humalog ™ (Eli Lily); Insulin Lispro (Eli Lily) | Hypoglycemic Agents | For treatment of diabetes (type I and II) | 154795 |
| Insulin recombinant | Novolin R ™ (Novo Nordisk) | Hypoglycemic Agents | For treatment of diabetes (type I and II) | 156308 |
| Insulin, porcine | Iletin II ™ | Hypoglycemic Agents | For the treatment of diabetes (type I and II) | 156308 |
| Interferon | | | | |
| Interferon Alfa-2a, Recombinant | Roferon A ™ (Hoffmann-La Roche Inc); Veldona ™ (Amarillo Biosciences) | Antineoplastic Agents; Antiviral Agents | For treatment of chronic hepatitis C, hairy cell leukemia, AIDS-related Kaposi's sarcoma, and chronic myelogenous leukemia. Also for the treatment of oral warts arising from HIV infection. | 57759 |
| Interferon Alfa-2b, Recombinant | Intron A ™ (Schering Corp) | Antineoplastic Agents; Antiviral Agents; Immunomodulatory Agents | For the treatment of hairy cell leukemia, malignant melanoma, and AIDS-related Kaposi's sarcoma. | 57759 |
| Interferon alfacon-1 | Advaferon ™; Infergen ™ (InterMune Inc) | Antineoplastic Agents; Antiviral Agents; Immunomodulatory Agents | For treatment of hairy cell leukemia, malignant melanoma, and AIDS-related Kaposi's sarcoma | 57759 |
| Interferon alfa-n1 | Wellferon ™ (GlaxoSmithKline) | Antiviral Agents; Immunomodulatory Agents | For treatment of venereal or genital warts caused by the Human Papilloma Virus | 57759 |
| Interferon alfa-n3 | Alferon ™ (Interferon Sciences Inc.); Alferon LDO ™; Alferon N Injection ™ | Antineoplastic Agents; Antiviral Agents; Immunomodulatory Agents | For the intralesional treatment of refractory or recurring external condylomata cuminate. | 57759 |
| Interferon beta-1b | Betaseron ™ (Chiron Corp) | Antiviral Agents; Immunomodulatory Agents | For treatment of relapsing/remitting multiple sclerosis | 57759 |

TABLE 1A-continued

Therapeutic Agent List

| Generic Name | Brands (Companies) | Category | Indication | Molecular Weight |
|---|---|---|---|---|
| Interferon gamma-1b | Actimmune ™; Actimmune ™ (InterMune Inc) | Antiviral Agents; Immunomodulatory Agents | For treatment of Chronic granulomatous disease, Osteopetrosis | 37835 |
| Lapatinib | | Tyrosine Kinase Inhibitors | | 581 |
| Lepirudin | Refludan ™ | Anticoagulants; Antithrombotic Agents; Fibrinolytic Agents | For the treatment of heparin-induced thrombocytopenia | 70037 |
| Lestaurtinib | | Tyrosine Kinase Inhibitors | | 439 |
| Leuprolide | Eligard ™ (Atrix Labs/QLT Inc) | Anti-Estrogen Agents; Antineoplastic Agents | For treatment of prostate cancer, endometriosis, uterine fibroids and premature puberty | 37731 |
| Lutropin alfa | Luveris ™ (Serono) | Fertility Agents | For treatment of female infertility | 78617 |
| Mecasermin | Increlex ™; Increlex ™ (Tercica); Iplex | | For the long-term treatment of growth failure in pediatric patients with Primary IGFD or with GH gene deletion who have developed neutralizing antibodies to GH. It is not indicated to treat Secondary IGFD resulting from GH deficiency, malnutrition, hypoth | 154795 |
| Menotropins | Repronex ™ | Fertility Agents | For treatment of female infertility | 78617 |
| Methotrexate | | Immunomodulatory | Uveitis, DME | |
| mTOR inhibitors | | | | |
| Muromonab | Orthoclone OKT3 ™ (Ortho Biotech) | Immunomodulatory Agents; Immunosuppressive Agents | For treatment of organ transplant recipients, prevention of organ rejection | 23148 |
| Natalizumab | Tysabri ™ | Immunomodulatory Agents | For treatment of multiple sclerosis. | 115334 |
| Nepafenac | | Cyclooxygenase Inhibitors | | |
| Nesiritide | Natrecor ™ | Cardiac drugs | For the intravenous treatment of patients with acutely decompensated congestive heart failure who have dyspnea at rest or with minimal activity. | 118921 |
| Nilotinib | | Tyrosine Kinase Inhibitors | | 530 |
| NS398 | | Cyclooxygenase Inhibitors | | |
| Octreotide | Atrigel ™; Longastatin ™; Sandostatin ™; Sandostatin LAR ™; Sandostatin LAR ™ (Novartis) | Anabolic Agents; Antineoplastic Agents, Hormonal; Gastrointestinal Agents; Hormone Replacement Agents | For treatment of acromegaly and reduction of side effects from cancer chemotherapy | 42687 |
| Omalizumab | Xolair ™ (Genentech Inc) | Anti-Asthmatic Agents; Immunomodulatory Agents | For treatment of asthma caused by allergies | 29596 |
| Oprelvekin | Neumega ™; Neumega ™ (Genetics Institute Inc) | Coagulants; Thrombotics | Increases reduced platelet levels due to chemotherapy | 45223 |
| OspA lipoprotein | LYMErix ™ (SmithKline Beecham) | Vaccines | For prophylactic treatment of Lyme Disease | 95348 |
| OT-551 | (Othera) | Anti-oxidant eyedrop | AMD | |
| Oxytocin | Oxytocin ™ (BAM Biotech); Pitocin ™ (Parke-Davis); Syntocinon ™ (Sandoz) | Anti-tocolytic Agents; Labor Induction Agents; Oxytocics | To assist in labor, elective labor induction, uterine contraction induction | 12722 |

TABLE 1A-continued

Therapeutic Agent List

| Generic Name | Brands (Companies) | Category | Indication | Molecular Weight |
|---|---|---|---|---|
| Palifermin | Kepivance ™ (Amgen Inc) | Antimucositis Agents | For treatment of mucositis (mouth sores) | 138885 |
| Palivizumab | Synagis ™ | Antiviral Agents | For treatment of respiratory diseases casued by respiratory syncytial virus | 63689 |
| Panitumumab | Vectibix ™; Vectibix ™ (Amgen) | Antineoplastic Agents | For the treatment of EGFR-expressing, metastatic colorectal carcinoma with disease progression on or following fluoropyrimidine-, oxaliplatin-, and irinotecan-containing chemotherapy regimens. | 134279 |
| PDGF inhibitor | (Jerini Ophthalmic); (Ophthotech) | Inhibitors of PDGF | AMD | |
| PEDF (pigment epithelium derived factor) | | | | |
| Pegademase bovine | Adagen ™ (Enzon Inc.) | Enzyme Replacement Agents | For treatment of adenosine deaminase deficiency | 36512 |
| Pegaptanib | Macugen ™ | Oligonucleotide | For the treatment of neovascular (wet) age-related macular degeneration. | 103121 |
| Pegaspargase | Oncaspar ™ (Enzon Inc) | Antineoplastic Agents | For treatment of acute lymphoblastic leukemia | 132.118 |
| Pegfilgrastim | Neulasta ™ (Amgen Inc.) | Anti-Infective Agents; Antineutropenic Agents; Immunomodulatory Agents | Increases leukocyte production, for treatment in non-myeloid cancer, neutropenia and bone marrow transplant | 28518 |
| Peginterferon alfa-2a | Pegasys ™ (Hoffman-La Roche Inc) | Antineoplastic Agents; Antiviral Agents; Immunomodulatory Agents | For treatment of hairy cell leukemia, malignant melanoma, and AIDS-related Kaposi's sarcoma. | 57759 |
| Peginterferon alfa-2b | PEG-Intron (Schering Corp); Unitron PEG ™ | Antineoplastic Agents; Antiviral Agents; Immunomodulatory Agents | For the treatment of chronic hepatitis C in patients not previously treated with interferon alpha who have compensated liver disease and are at least 18 years of age. | 57759 |
| Pegvisomant | Somavert ™ (Pfizer Inc) | Anabolic Agents; Hormone Replacement Agents | For treatment of acromegaly | 71500 |
| Pentoxifylline | | | | |
| Perindozril | | ACE Inhibitors | | |
| Pimecrolimus | | Limus Immunophilin Binding Compounds | | |
| PKC (protein kinase C) inhibitors | | | | |
| POT-4 | Potentia/Alcon | Complement Cascade Inhibitor (Factor C3) | AMD | |
| Pramlintide | Symlin ™; Symlin ™ (Amylin Pharmaceuticals) | | For the mealtime treatment of Type I and Type II diabetes in combination with standard insulin therapy, in patients who have failed to achieve adequate glucose control on insulin monotherapy. | 16988 |

TABLE 1A-continued

Therapeutic Agent List

| Generic Name | Brands (Companies) | Category | Indication | Molecular Weight |
|---|---|---|---|---|
| Proteosome inhibitors | Velcade ™ | | Proteosome inhibitors | |
| Pyrrolidine | | | | |
| Quinopril | | ACE Inhibitors | | |
| Ranibizumab | Lucentis ™ | | For the treatment of patients with neovascular (wet) age-related macular degeneration. | 27043 |
| Rapamycin (siroliums) | (MacuSight) | Limus Immunophilin Binding Compounds | AMD | |
| Rasburicase | Elitek ™; Elitek ™ (Sanofi-Synthelabo Inc); Fasturtec ™ | Antihyperuricemic Agents | For treatment of hyperuricemia, reduces elevated plasma uric acid levels (from chemotherapy) | 168.11 |
| Reteplase | Retavase ™ (Centocor); Retavase ™ (Roche) | Thrombolytic Agents | For lysis of acute pulmonary emboli, intracoronary emboli and management of myocardial infarction | 54732 |
| Retinal stimulant | Neurosolve ™ (Vitreoretinal Technologies) | Retinal stimulants | AMD | |
| Retinoid(s) | | | | |
| Rituximab | MabThera ™; Rituxan ™ | Antineoplastic Agents | For treatment of B-cell non-Hodgkins lymphoma (CD20 positive) | 33078 |
| RNAI (RNA interference of angiogenic factors) | | | | |
| Rofecoxib | Vioxx ™; Ceoxx ™; Ceeoxx ™ (Merck & Co.) | Cyclooxygenase Inhibitors | | |
| Rosiglitazone | | Thiazolidinediones | | |
| Ruboxistaurin | Eli Lilly | Protein Kinase C (PKC)-b Inhibitor | DME, diabetic peripheral retinopathy | 469 |
| Salmon Calcitonin | Calcimar ™; Miacalcin ™ (Novartis) | Antihypocalcemic Agents; Antiosteoporotic Agents; Bone Density Conservation Agents | For the treatment of post-menopausal osteoporosis | 57304 |
| Sargramostim | Immunex ™; Leucomax ™ (Novartis); Leukine ™; Leukine ™ (Berlex Laboratories Inc) | Anti-Infective Agents; Antineoplastic Agents; Immunomodulatory Agents | For the treatment of cancer and bone marrow transplant | 46207 |
| SAR 1118 | SARCode | Immunomodulatory Agent | Dry eye, DME, conjunctivitis | |
| SDZ-RAD | | Limus Immunophilin Binding Compounds | | |
| Secretin | SecreFlo ™; Secremax ™, SecreFlo ™ (Repligen Corp) | Diagnostic Agents | For diagnosis of pancreatic exocrine dysfunction and gastrinoma | 50207 |
| Selective inhibitor of the factor 3 complement cascade | | | | |
| Selective inhibitor of the factor 5 complement cascade | | | | |
| Semaxanib | | Tyrosine Kinase Inhibitors | | 238 |
| Sermorelin | Geref ™ (Serono Pharma) | Anabolic Agents; Hormone Replacement Agents | For the treatment of dwarfism, prevention of HIV-induced weight loss | 47402 |
| Serum albumin iodinated | Megatope ™ (IsoTex Diagnostics) | Imaging Agents | For determination of total blood and plasma volumes | 39000 |
| SF1126 | Semafore | PI3k/mTOR Inhibition | AMD, DME | |
| Sirolimus reformulation (rapamycin) | (MacuSight) | Limus Immunophilin Binding Compounds | AMD | |
| siRNA molecule synthetic, FTP-801i-14 | (Quark Pharmaceuticals) | siRNA molecule synthetic | AMD | |

TABLE 1A-continued

Therapeutic Agent List

| Generic Name | Brands (Companies) | Category | Indication | Molecular Weight |
|---|---|---|---|---|
| Somatropin recombinant | BioTropin ™ (Biotech General); Genotropin ™ (Pfizer); Humatrope ™ (Eli Lilly); Norditropin ™ (Novo Nordisk); Nutropin ™ (Genentech Inc.); NutropinAQ ™ (Genentech Inc.); Protropin ™ (Genentech Inc.); Saizen ™ (Serono SA); Serostim ™; Serostim ™ (Serono SA); Tev-Tropin ™ (GATE) | Anabolic Agents; Hormone Replacement Agents | For treatment of dwarfism, acromegaly and prevention of HIV-induced weight loss | 71500 |
| Squalamine | | | | |
| Streptokinase | Streptase ™ (Aventis Behringer GmbH) | Thrombolytic Agents | For the treatment of acute evolving transmural myocardial infarction, pulmonary embolism, deep vein thrombosis, arterial thrombosis or embolism and occlusion of arteriovenous cannulae | 90569 |
| Sunitinib | | Tyrosine Kinase Inhibitors | | 398 |
| TA106 | Taligen | Complement Cascade Inhibitor (Factor B) | AMD | |
| Tacrolimus | | Limus Immunophilin Binding Compounds | | |
| Tenecteplase | TNKase ™ (Genentech Inc) | Thrombolytic Agents | For treatment of myocardial infarction and lysis of intracoronary emboli | 54732 |
| Teriparatide | Apthela ™; Forsteo ™; Forteo ™; Fortessa ™; Opthia ™; Optia ™; Optiah ™; Zalectra ™; Zelletra ™ | Bone Density Conservation Agents | For the treatment of osteoporosis in men and postmenopausal women who are at high risk for having a fracture. Also used to increase bone mass in men with primary or hypogonadal osteoporosis who are at high risk for fracture. | 66361 |
| Tetrathiomolybdate | | | | |
| Thalidomide | Celgene | Anti-inflammatory, Anti-proliferative | Uveitis | |
| Thyrotropin Alfa | Thyrogen ™ (Genzyme Inc) | Diagnostic Agents | For detection of residual or recurrent thyroid cancer | 86831 |
| Tie-1 and Tie-2 kinase inhibitors | | | | |
| Toceranib | | Tyrosine Kinase Inhibitors | | 396 |
| Tositumomab | Bexxar ™ (Corixa Corp) | Antineoplastic Agents | For treatment of non-Hodgkin's lymphoma (CD20 positive, follicular) | 33078 |
| TPN 470 analogue | | | | |
| Trastuzumab | Herceptin ™ (Genentech) | Antineoplastic Agents | For treatment of HER2-positive pulmonary breast cancer | 137912 |
| Triamcinolone acetonide | Triesence ™ | Glucocorticoid | DME, For treatment of inflammation of the retina | 435 |
| Troglitazone | | Thiazolidinediones | | |
| Tumistatin | | | | |
| Urofollitropin | Fertinex ™ (Serono S.A.) | Fertility Agents | For treatment of female infertility | 78296 |
| Urokinase | Abbokinase ™; Abbokinase ™ (Abbott Laboratories) | Thrombolytic Agents | For the treatment of pulmonary embolism, coronary artery | 90569 |

TABLE 1A-continued

Therapeutic Agent List

| Generic Name | Brands (Companies) | Category | Indication | Molecular Weight |
|---|---|---|---|---|
| | | | thrombosis and IV catheter clearance | |
| Vandetanib | | Tyrosine Kinase Inhibitors | | 475 |
| Vasopressin | Pitressin ™; Pressyn ™ | Antidiuretics; Oxytocics; Vasoconstrictor Agents | For the treatment of enuresis, polyuria, diabetes insipidus, polydipsia and oesophageal varices with bleeding | 46800 |
| Vatalanib | | Tyrosine Kinase Inhibitors | | 347 |
| VEGF receptor kinase inhibitor | | | | |
| VEGF Trap | Aflibercept ™ (Regneron Pharmaceuticals, Bayer HealthCare AG) | Genetically Engineered Antibodies | DME, cancer, retinal vein occlusion, choroidal neovascularization, delay wound healing, cancer treatment | 96600 |
| Visual Cycle Modulator ACU-4229 | (Acucela) | Visual Cycle Modulator | AMD | |
| Vitamin(s) | | | | |
| Vitronectin receptor antagonists | | | | |
| Volociximab | Ophthotech | alpha5beta1 Integrin Inhibitor | AMD | |
| XL765 | Exelixis/Sanofi-Aventis | PI3k/mTOR Inhibition | AMD, DME | |

What is claimed is:

1. An apparatus to insert an implantable therapeutic device into a patient, the apparatus extending along a longitudinal axis from a proximal end of the apparatus to a distal end of the apparatus, the apparatus comprising:
   a proximal handle; and
   a distal placement portion coupled to the proximal handle and configured to hold the implantable therapeutic device, the distal placement portion comprising:
     a first side having a first engagement structure at a distal end of the first side, the first engagement structure being substantially c-shaped and configured to surround at least a first portion of a proximal end region of the implantable therapeutic device;
     a second, opposite side having a second engagement structure at a distal end of the second side, the second engagement structure being substantially c-shaped and configured to surround at least a second, opposite portion of the proximal end region of the implantable therapeutic device,
     wherein each of the first and second engagement structures comprises:
       a distal-facing surface;
       a proximal-facing surface opposite the distal-facing surface that extends substantially orthogonal to the longitudinal axis of the apparatus; and
       an inward-facing protrusion tapering distally towards the distal-facing surface; and
     at least one guide surface located proximal to the first and second engagement structures and angled obliquely relative to the longitudinal axis from the proximal end towards the distal end of the apparatus.

2. The apparatus of claim 1, further comprising the implantable therapeutic device, wherein the implantable therapeutic device includes a retention structure at the proximal end region comprising a narrow portion, a shoulder and a proximal extension.

3. The apparatus of claim 2, wherein the inward-facing protrusion and the proximal-facing surface of the first and second engagement structures are shaped and sized to engage a portion of the retention structure.

4. The apparatus of claim 3, wherein each of the inward-facing protrusions is configured to extend into the narrow portion.

5. The apparatus of claim 4, wherein when the inward-facing protrusions extend into the narrow portion, the proximal-facing surface extending substantially orthogonal engages a distal surface of the proximal extension and a distal surface of each protrusion engages the shoulder.

6. The apparatus of claim 2, wherein the distal placement portion further comprises a recess through which a proximal surface of the proximal extension is accessible.

7. The apparatus of claim 6, wherein the at least one guide surface is configured to support and maintain alignment of a needle extending at an angle oblique to a longitudinal axis of the implantable device prior to penetration of the implantable device by the needle, wherein the longitudinal axis of the implantable device and the longitudinal axis of the apparatus are coaxially aligned.

8. The apparatus of claim 7, wherein the needle includes a connector and wherein the at least one guide surface has a concave shape complimentary to a convex shape of the connector to mate with the connector and maintain alignment of the needle relative to the implantable device.

9. The apparatus of claim 1, wherein the proximal handle includes first and second opposing handles extending on opposite sides of the longitudinal axis, wherein the first opposing handle is coupled to a proximal end of the first side and the second opposing handle is coupled to a proximal end of the second side.

10. The apparatus of claim 9, wherein the first and second opposing handles are configured to urge the first side and the second side toward each other to engage the implantable device when the first and second opposing handles move away from the axis and to urge the first side and the second side away from each other to release the implantable device when the first and second opposing handles move toward the axis.

11. The apparatus of claim 9, wherein the first and second opposing handles are configured to urge the first side and the second side toward each other to engage the implantable device when the first and second opposing handles move toward the axis and to urge the first side and the second side away from each other to release the implantable device when the first and second opposing handles move away from the axis.

12. A kit to treat a patient, the kit comprising:
an insertion apparatus of claim 1;
an implantable therapeutic device; and
packaging to contain the insertion apparatus and the implantable therapeutic device.

13. The apparatus of claim 1, wherein the at least one guide surface comprises a plurality of recessed surfaces, each of the plurality of recessed surfaces angled obliquely relative to the longitudinal axis from the proximal end towards the distal end of the apparatus.

14. The apparatus of claim 13, wherein the plurality of recessed surfaces comprises a first proximal guide surface, a first intermediate guide surface and a first distal guide surface on the first side of the distal placement portion and a second proximal guide surface, a second intermediate guide surface and a second distal guide surface on the second side, opposite side of the distal placement portion.

15. The apparatus of claim 13, wherein when the first and second engagement structures are surrounding the proximal end region of the implantable therapeutic device, an upper surface of the implantable therapeutic device remains exposed and external to the apparatus.

16. The apparatus of claim 15, wherein the plurality of recessed surfaces are arranged to provide a visual reference to a user advancing a needle and guide the needle toward the upper surface of the implantable therapeutic device.

17. The apparatus of claim 1, wherein the distal placement portion further comprises a front side and a back side located opposite the front side, wherein the at least one guide surface is located on the front side of the distal placement portion.

18. The apparatus of claim 17, wherein the first engagement structure and the second engagement structure each extends upwards away from the longitudinal axis and away from the at least one guide surface on the front side of the distal placement portion.

19. The apparatus of claim 17, wherein the at least one guide surface on the front side tapers from the proximal end towards the distal end of the apparatus forming a first angle relative to the longitudinal axis, and wherein the back side of the distal placement portion tapers from the proximal end towards the distal end of the apparatus forming a second angle relative to the longitudinal axis, wherein the first angle is different than the second angle.

20. The apparatus of claim 17, wherein the at least one guide surface on the front side has a concave shape and the back side has a substantially convex shape.

21. The apparatus of claim 1, wherein the at least one guide surface has a concave shape to complement a convex shape of a needle connector.

* * * * *